(12) United States Patent
Ellis

(10) Patent No.: US 9,693,603 B2
(45) Date of Patent: Jul. 4, 2017

(54) SETS OFORTHOTIC INSERTS OR OTHER FOOTWEAR INSERTS WITH PROGRESSIVE CORRECTIONS AND AN INTERNAL SIPE

(71) Applicant: Frampton E. Ellis, Jasper, FL (US)

(72) Inventor: Frampton E. Ellis, Jasper, FL (US)

( * ) Notice: Subject to any disclaimer, the term of this patent is extended or adjusted under 35 U.S.C. 154(b) by 111 days.

(21) Appl. No.: 14/449,979

(22) Filed: Aug. 1, 2014

(65) Prior Publication Data

US 2015/0013183 A1    Jan. 15, 2015

Related U.S. Application Data

(63) Continuation of application No. 12/163,332, filed on Jun. 27, 2008, now Pat. No. 8,819,961.
(Continued)

(51) Int. Cl.
*A43B 13/38* (2006.01)
*A43B 7/14* (2006.01)
(Continued)

(52) U.S. Cl.
CPC ............ *A43B 13/386* (2013.01); *A43B 7/148* (2013.01); *A43B 7/1415* (2013.01);
(Continued)

(58) Field of Classification Search
CPC ..... A43B 13/386; A43B 13/186; A43B 13/14; A43B 13/188; A43B 13/38; A43B 13/20;
(Continued)

(56) References Cited

U.S. PATENT DOCUMENTS 3,543,765 A    12/1970  Alzner
3,642,563 A *  2/1972   Davis .................. A43B 5/10
                                                          156/307.5
(Continued)

FOREIGN PATENT DOCUMENTS

WO    2006058013 A2    6/2006

OTHER PUBLICATIONS

Complete file history for U.S. Appl. No. 12/163,332.
Align Technology, Inc. "Invisalign, Learn How to Smile Again" (informational packet), 16 pages.

*Primary Examiner* — Anna Kinsaul
*Assistant Examiner* — Jocelyn Wu
(74) *Attorney, Agent, or Firm* — Mendelsohn Dunleavy, P.C.

(57) ABSTRACT

Orthotics or other footwear inserts including a set of separate and incrementally different inserts sized and adapted for a right and/or left foot. One such insert in said set has a first corrective structure and at least another such insert has a second corrective structure. The second corrective structure including at least an incremental change in one or more of curvature, thickness and firmness of at least one sidemost portion of said insert in said set as compared to the first corrective structure and a corrective structure of each other said insert in said set. The inserts in the set have a progressive sequence based on the increase or decrease in one of the curvature, thickness and firmness, are adapted to be worn one at a time for a period of time sequentially based on the progressive sequence and also include at least one internal sipe.

23 Claims, 21 Drawing Sheets

Related U.S. Application Data

(60) Provisional application No. 60/929,485, filed on Jun. 29, 2007, provisional application No. 60/929,663, filed on Jul. 6, 2007, provisional application No. 60/929,672, filed on Jul. 9, 2007, provisional application No. 60/935,555, filed on Aug. 17, 2007.

(51) Int. Cl.
| | | |
|---|---|---|
| *A43B 13/14* | (2006.01) | |
| *A43B 13/18* | (2006.01) | |
| *A43B 17/00* | (2006.01) | |
| *A43B 5/14* | (2006.01) | |
| *A61F 5/14* | (2006.01) | |

(52) U.S. Cl.
CPC ............ *A43B 7/1465* (2013.01); *A43B 13/14* (2013.01); *A43B 13/186* (2013.01); *A43B 13/188* (2013.01); *A43B 13/38* (2013.01); *A43B 17/00* (2013.01); *A61F 5/14* (2013.01)

(58) Field of Classification Search
CPC ..... A43B 7/1415; A43B 7/1465; A43B 7/148; A43B 17/00; A61F 5/14
See application file for complete search history.

(56) References Cited

U.S. PATENT DOCUMENTS

| | | | |
|---|---|---|---|
| 4,771,394 A | 9/1988 | Cavanagh | |
| 5,317,819 A | 6/1994 | Ellis | |
| 5,353,459 A * | 10/1994 | Potter | A43B 17/03 12/146 R |
| 5,438,768 A * | 8/1995 | Bauerfeind | A43B 7/1425 36/165 |
| 5,544,429 A | 8/1996 | Ellis | |
| 5,718,063 A | 2/1998 | Yamashita et al. | |
| 5,755,001 A * | 5/1998 | Potter | A43B 21/28 12/142 P |
| 5,909,948 A | 6/1999 | Ellis | |
| 6,023,857 A | 2/2000 | Vizy et al. | |
| 6,038,790 A | 3/2000 | Pyle et al. | |
| 6,092,311 A * | 7/2000 | MacNamara | A43B 1/0036 36/100 |
| 6,115,941 A | 9/2000 | Ellis | |
| 6,115,945 A | 9/2000 | Ellis | |
| 6,163,982 A | 12/2000 | Ellis | |
| 6,295,744 B1 | 10/2001 | Ellis | |
| 6,308,439 B1 | 10/2001 | Ellis | |
| 6,314,662 B1 | 11/2001 | Ellis | |
| 6,360,453 B1 | 3/2002 | Ellis | |
| 6,360,457 B1 | 3/2002 | Qui et al. | |
| 6,408,543 B1 | 6/2002 | Erickson et al. | |
| 6,463,612 B1 * | 10/2002 | Potter | A43B 13/20 12/146 B |
| 6,487,795 B1 | 12/2002 | Ellis | |
| 6,584,706 B1 | 7/2003 | Ellis | |
| 6,591,519 B1 | 7/2003 | Ellis | |
| 6,609,312 B1 | 8/2003 | Ellis | |
| 6,629,376 B1 | 10/2003 | Ellis | |
| 6,662,470 B2 | 12/2003 | Ellis | |
| 6,675,498 B1 | 1/2004 | Ellis | |
| 6,675,499 B2 | 1/2004 | Ellis | |
| 6,708,424 B1 | 3/2004 | Ellis, III | |
| 6,722,059 B2 | 4/2004 | Robinson, Jr. et al. | |
| 6,729,046 B2 | 5/2004 | Ellis | |
| 6,748,674 B2 | 6/2004 | Ellis | |
| 6,763,616 B2 | 7/2004 | Ellis | |
| 6,789,331 B1 | 9/2004 | Ellis | |
| 6,796,056 B2 | 9/2004 | Swigart | |
| 6,810,606 B1 | 11/2004 | Ellis | |
| 6,880,266 B2 | 4/2005 | Schoenborn et al. | |
| 6,918,197 B2 | 7/2005 | Ellis | |
| 6,971,193 B1 * | 12/2005 | Potter | A43B 13/203 36/141 |
| 6,990,756 B1 * | 1/2006 | Johnson | A43B 7/142 36/155 |
| 7,010,869 B1 | 3/2006 | Ellis | |
| 7,082,697 B2 | 8/2006 | Ellis | |
| 7,093,379 B2 | 8/2006 | Ellis | |
| 7,174,658 B2 | 2/2007 | Ellis | |
| 7,200,955 B2 | 4/2007 | Foxen | |
| 7,234,249 B2 | 6/2007 | Ellis | |
| 7,249,425 B2 | 7/2007 | Wang | |
| 7,287,341 B2 | 10/2007 | Ellis | |
| 7,334,350 B2 | 2/2008 | Ellis | |
| 7,334,356 B2 | 2/2008 | Ellis | |
| 7,546,699 B2 | 6/2009 | Ellis, III | |
| 7,721,467 B2 | 5/2010 | Cheskin et al. | |
| 8,819,961 B1 | 9/2014 | Ellis | |
| 2002/0050080 A1 | 5/2002 | Vasyli | |
| 2004/0181971 A1 | 9/2004 | Turkbas et al. | |
| 2006/0080869 A1 * | 4/2006 | Johnson | A43B 7/142 36/155 |
| 2006/0107553 A1 * | 5/2006 | Clark | A43B 3/26 36/97 |
| 2007/0271817 A1 | 11/2007 | Ellis | |
| 2008/0000108 A1 | 1/2008 | Ellis | |
| 2008/0005931 A1 | 1/2008 | Ellis | |
| 2008/0022556 A1 | 1/2008 | Ellis | |
| 2008/0086916 A1 | 4/2008 | Ellis | |
| 2008/0127518 A1 * | 6/2008 | Byrne | A43B 3/26 36/97 |

\* cited by examiner

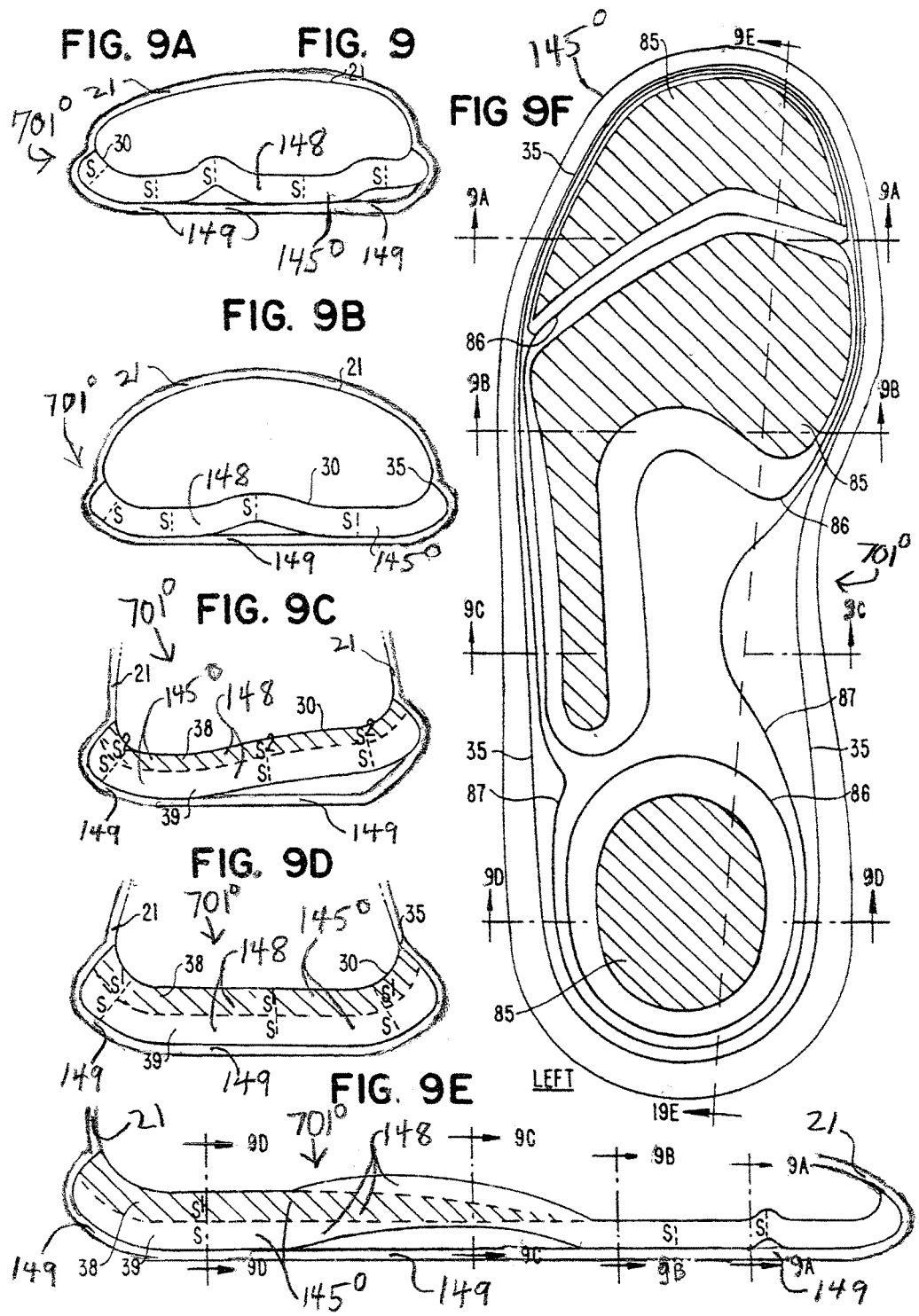

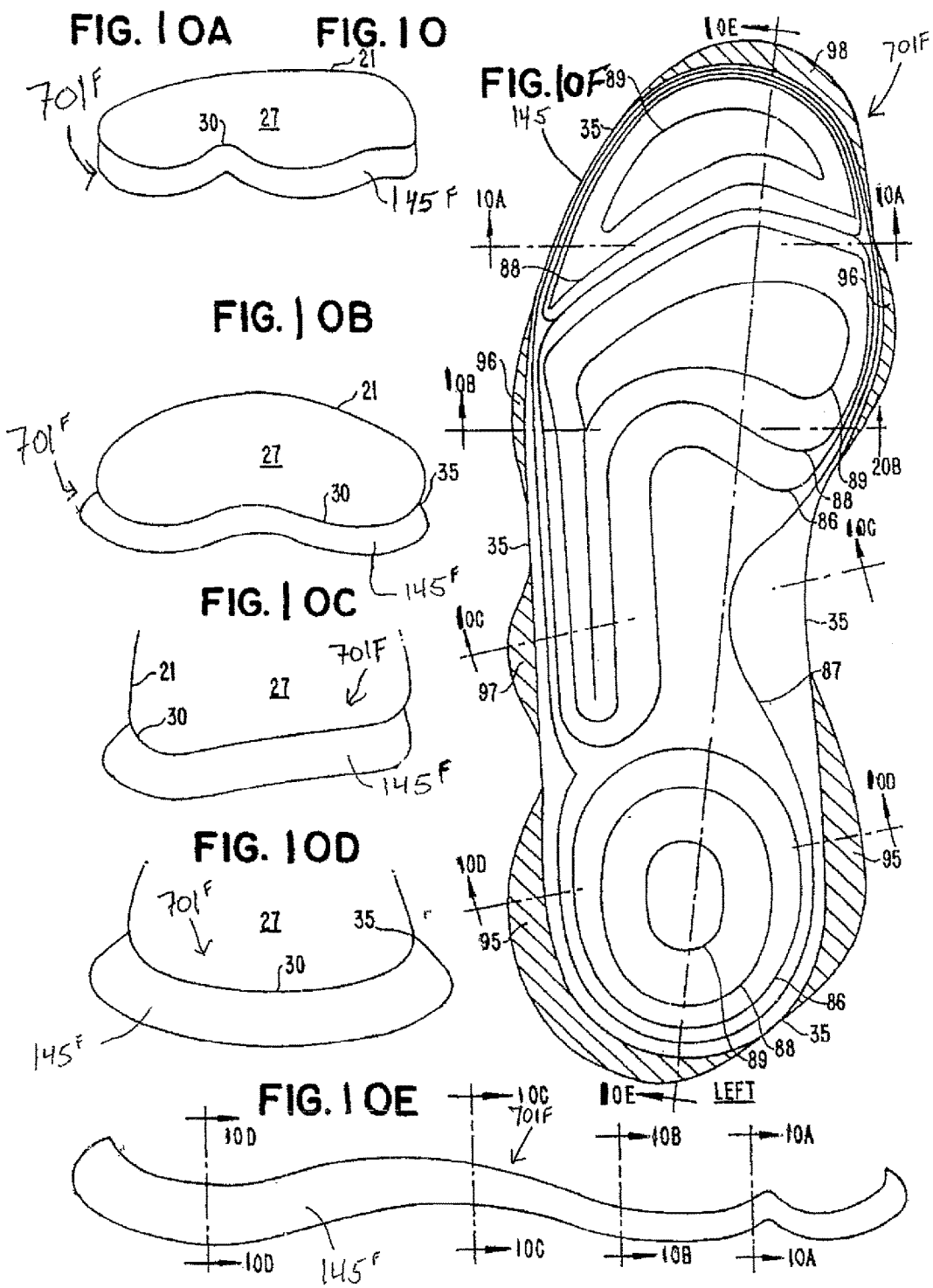

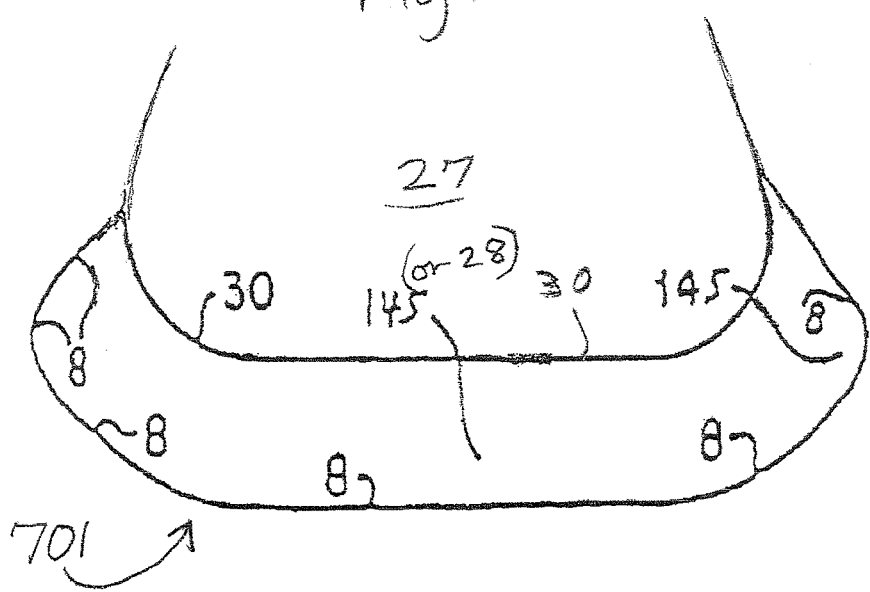

FIG. 11D
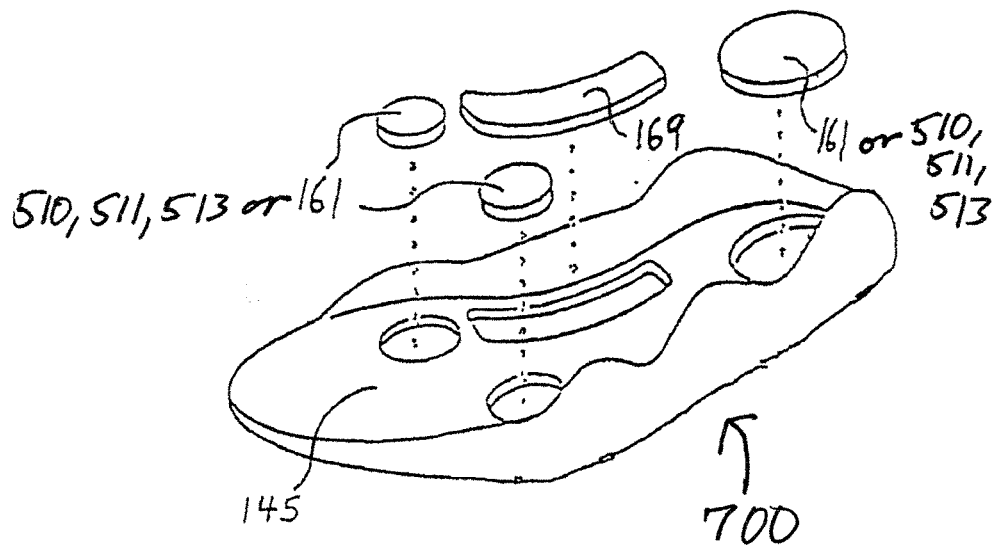
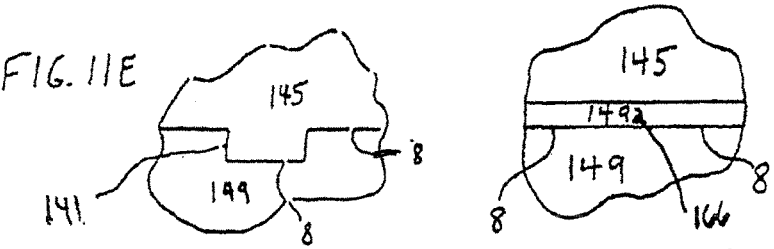
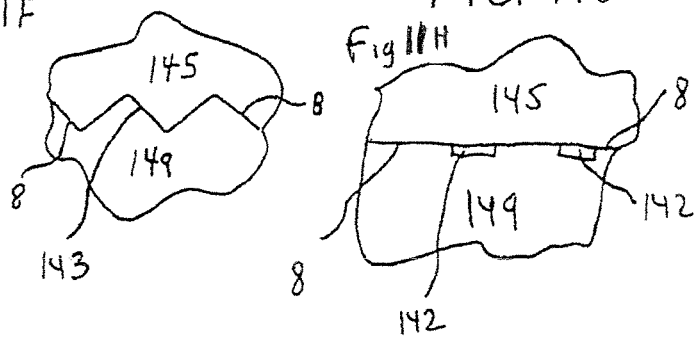

SETS OF ORTHOTIC INSERTS OR OTHER FOOTWEAR INSERTS WITH PROGRESSIVE CORRECTIONS AND AN INTERNAL SIPE

CROSS-REFERENCE TO RELATED APPLICATIONS

This application is a continuation of U.S. non-provisional application Ser. No. 12/163,332 filed Jun. 27, 2008: which claims the benefits of U.S. provisional application No. 60/929,485 filed Jun. 29, 2007; U.S. provisional application No. 60/929,663 filed Jul. 6, 2007; U.S. provisional application No. 60/929,672 filed Jul. 9, 2007; and U.S. provisional application No. 60/935,555 filed Aug. 17, 2007.

BACKGROUND OF THE INVENTION

1. Field of the Invention

The present invention relates to sets of inserts, footwear soles and/or orthotics which employ a progression of corrective structures.

2. Brief Description of the Background of the Invention

Footwear soles and orthotics can be improved by using a progression of corrections in a series of soles or orthotics (or both) or inserts thereto that are used sequentially by a wearer. The progression of footwear sole and/or orthotic corrections can use, for example, incremental improvements in foot position (starting from an untreated, original state) by progressing through a series of incremental intermediate states, each controlled by the form of a sole or orthotic with a incremental improvement compared to the previous state, to a final or corrected state. Thus, a major correction can be achieved over time through a progressive series of relatively minor changes better tolerated by a wearer and to which the bones and other structures of the foot can more safely adapt.

SUMMARY OF THE INVENTION

In one aspect, the invention relates to a footwear sole or an orthotic or combinations of both including a set of incrementally different inserts forming a progressive sequence. The progressive sequence includes inserts having corrective structures that are incrementally closer to a final corrective structure than a corrective structure of a previous insert in the sequence. The corrective structure of the inserts may change in one or more of shape, thickness and firmness of at least one portion of the at least one insert as compared to the previous insert in the sequence. Each of the inserts of the set is worn for a period of time in order of the progressive sequence as part of the footwear sole and/or orthotic.

In a second aspect, the invention relates to a set of incrementally different footwear soles or orthotics or combinations of both forming a progressive sequence. The progressive sequence includes at least one sole and/or orthotic that comprises a corrective structure that is incrementally closer to a final corrective structure than at least one of a previous sole and orthotic in the sequence. The corrective structure of the at least one sole and/or orthotic is provided by at least a change in at least one of a shape, thickness and firmness of at least one portion of the at least one sole and/or orthotic as compared to the previous sole and/or orthotic in the sequence. Each of the inserts of the set is worn for a period of time in order of the progressive sequence as part of the footwear sole and/or orthotic.

In a third aspect, the present invention relates to a footwear sole or an orthotic or combinations of both, comprising a set of incrementally different inserts forming a progressive sequence. The progressive sequence includes at least one insert comprising a corrective structure that is incrementally closer to a final corrective structure than at least one previous insert in the sequence. The corrective structure of the at least one insert is provided by at least a change in shape of at least one portion of the at least one insert as compared to the previous insert in the sequence. Each of the inserts of the set is worn for a period of time in order of the progressive sequence as part of the footwear sole and/or orthotic.

Each intermediate and final state of the correction process can have a separate set (typically, for right and left feet) of progressively corrective footwear soles or orthotics (or combinations of both) or inserts therefor, and can be made using any of the many forms of mechanical drawing or electronic design, including graphical or computer aided design/computer aided manufacturing (CAD/CAM) techniques. The original or uncorrected state of a foot or feet to be corrected can be determined by any conventional or new molding or scanning processes (laser, MRI, CT, mechanical, or other) or other measuring technique in an unloaded condition or with any load, like full or partial body weight, for example, and can be for a specific individual in a custom set (either prescribed by a medical, podiatric, or other professional or not prescriptive) or a standard set for similar categories of individuals (such as standard size and typical foot form, like a pronated or supinated foot position), also potentially prescribed or not. A wearer can be human or animal. The use of the invention can involve, for example, a static condition in adulthood or a dynamic condition like a progressive disease or growth, or any combination thereof. Any organic or inorganic growth or corrective process can also incorporate the invention.

The incremental intermediate states of the progressively corrected footwear soles or orthotics or inserts therefore can be of any finite number, with three or five or 10 or 15 or 20 being useful examples. Each corrective state (beginning, intermediate corrective increments, and final correct correction) can have a separate set of footwear soles or orthotics (including uppers of either) or both, each with improvements progressively closer to a final corrected state. Each set of progressively corrected footwear soles or orthotics can be worn for a limited period of time, such as a week or month, for example, while the final, corrected set can be used permanently, either full time or intermittently, like dental retainers, to maintain the corrected state. Monitoring and/or testing and/or new scanning of the wearer and the wearer's foot or feet can be done at any time while the progressively corrective footwear soles and/or orthotics are in use, and adjustment or replacement of the progressively corrected footwear soles and/or orthotics can occur as necessary. In general, the invention uses progressive or incremental corrections in a manner that is in some ways similar to Invisalign™ Orthodontic Appliances (a new form of braces known in the dental art).

Since walking and running involve different biomechanics, particularly during the support phase, the progressively corrective footwear soles and/or orthotics can be designed specifically for either form of locomotion (or for other forms of locomotion or exercise or sport, including those involving greater degrees of lateral motion).

The progressively corrected footwear sole or orthotic or inserts therefor can be or include an insole and/or midsole and/or midsole component, including a compartment or chamber or bladder (like for example Nike Air™) and/or outer sole (or bottom sole) and can include part or all of an upper, and the entire footwear or orthotic can be formed from one material suitable for soles (like Crocs™ or Waldies™ clog-like commercial examples) or from more than one material like a common modern athletic shoe well known in the prior art.

The progressively corrected footwear soles or orthotics or both can be a part or all of an otherwise conventional footwear sole or orthotic, or can be a removable midsole insert or removeable orthotic insert, although the applicant's previous footwear inventions based on the barefoot and described in previous patents and patent applications (from the '665 application incorporated herein later in this application) are preferred, including the applicant's removeable midsole insert or removable orthotic insert 145.

BRIEF DESCRIPTION OF THE DRAWINGS

FIGS. 9A-9F show multiple parallel plane cross section views of an initial or original orthotic insert $145^O$ and a final orthotic insert $145^F$ (or removable midsole insert $145^O$ or $145^F$). The upper 21 and bottomsole 149 can be integrated to form one piece such as is done in Classic Crocs™ or Waldies™.

FIGS. 10A-10F show multiple parallel plane cross section views of an initial or original orthotic insert $145^O$ and a final orthotic insert $145^F$ (or removable midsole insert $145^O$ or $145^F$). The orthotic insert $145^F$ can include a bottom sole 149 and upper 21, as in the embodiments of FIGS. 9A-9F, though not shown in these FIGS. 10A-10F. The embodiment of FIG. 10E includes a heel lift 38 though the heel lift 38 is not separately shown in FIG. 10E.

FIG. 11A shows a sole or orthotic insert 145 with a thermal-pressure moldable material, as viewed in a frontal plane cross section with the shoe or orthotic insert 145 in an upright, unloaded condition.

FIGS. 11B-H show other views from the '665 application including an example of the incremental correction 700 invention with the insert 145 and the applicant's 510 or 511 or 513 inventions. FIGS. 11B-11C also show frontal plane cross sections of the invention in an upright, unloaded condition.

DETAILED DESCRIPTION OF THE PREFERRED EMBODIMENTS

"Corrective structure" and "correction" are used interchangeably in this patent application with reference to an insert, footwear sole, orthotic, or portion thereof, to refer to the structure of the insert, footwear sole, orthotic, or portion thereof designed to provide a correction to an intended wearer.

Figure 1:
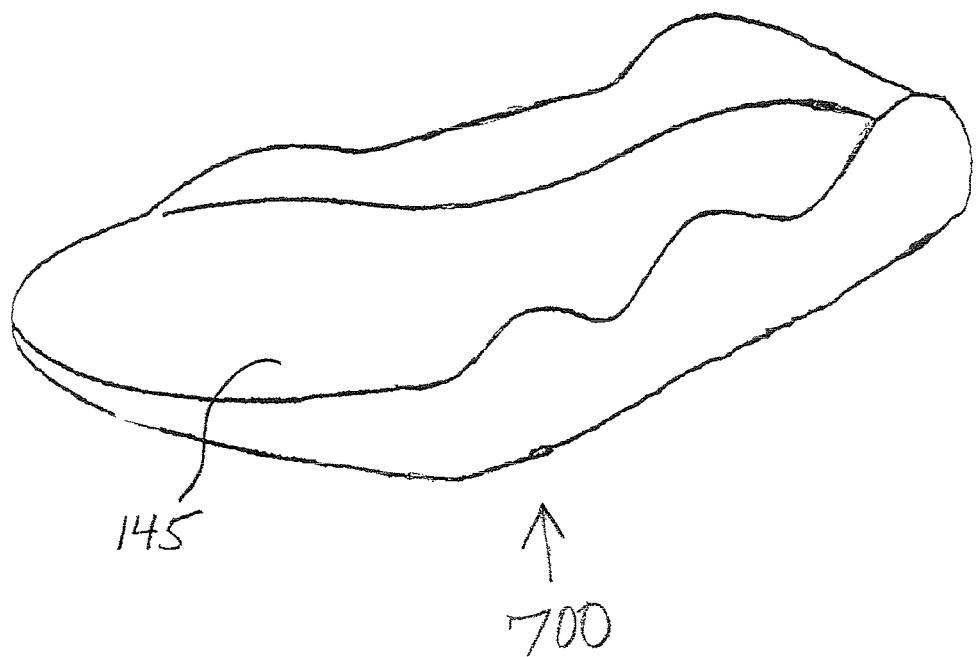
FIG. 1 is a perspective view of a footwear sole 22 or 28 or removeable midsole or orthotic insert 145 for a progressively corrected footwear sole or orthotic 700.

As an example embodiment, FIG. 1 shows a perspective view of the progressively corrected footwear sole or orthotic 700 in the specific form of a removable midsole or orthotic insert 145, which can be either a part or all of a footwear sole 28 or 22 or of an orthotic sole, and can include or incorporate all or part of a footwear or orthotic upper 21. The insert 145 is insertable into the footwear sole or orthotic by a wearer in the same manner in which a wearer conventionally inserts a foot into the footwear or orthotic.

Figure 2:
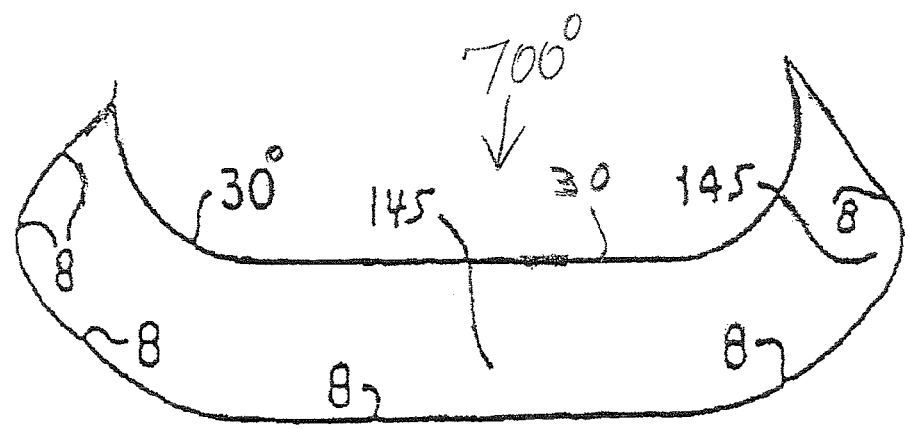
FIGS. 2-5 show an insert 145 with incrementally increasing inner or upper surfaces 30 for a progressively corrected footwear sole or orthotic 700, as viewed in a frontal plane cross section in an upright, unloaded condition.
Figure 11B:
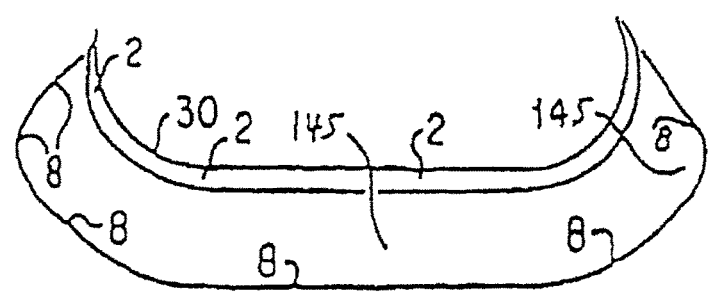

FIG. 2 shows of the removable midsole or orthotic insert 145 in an unloaded, upright frontal plane cross section, like FIG. 11B (without insole 2) of the applicant' U.S. application Ser. No. 11/282,665 filed Nov. 21, 2005, and published on Nov. 9, 2006, as Publication No. US 2006/0248749 A1, which is incorporated by reference herein in its entirety. FIG. 2 shows an original or starting inner or upper surface $30^O$ for a progressively corrected footwear sole or orthotic 700, shown as $700^O$.

Figure 3:
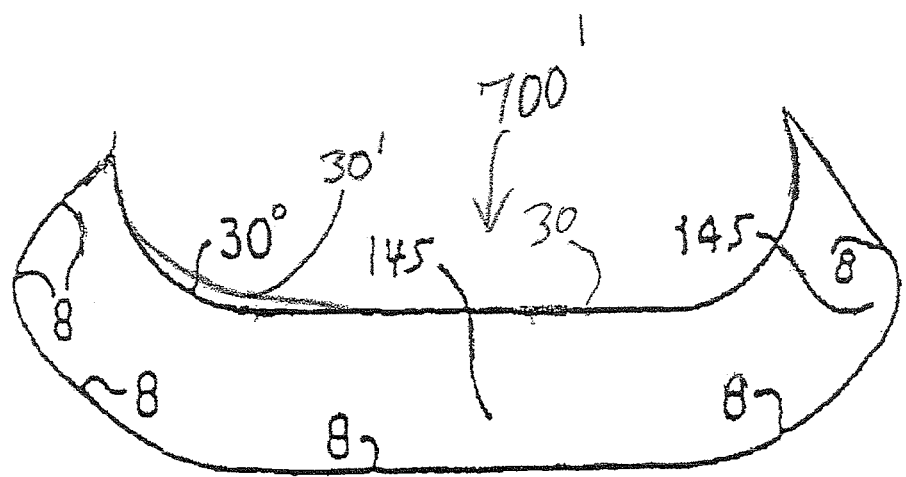
Figure 6:
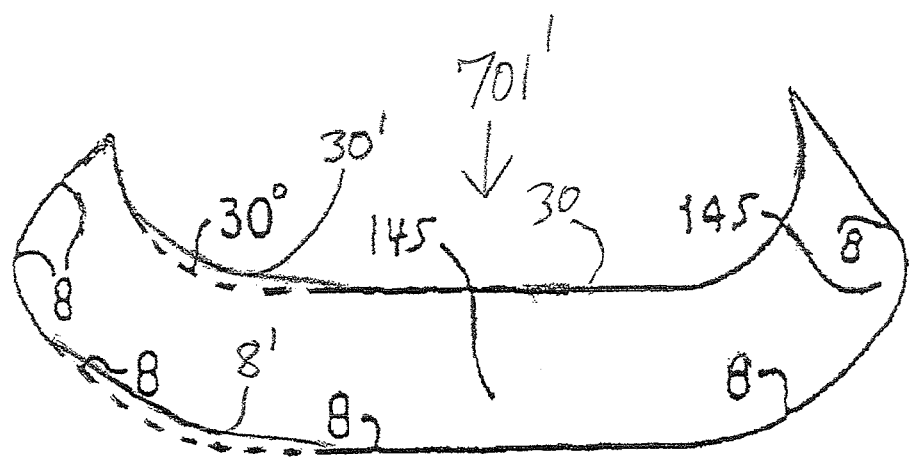
FIGS. 6-8 show an insert 145 with incrementally increasing inner or upper surfaces 30 and a lower surface 8 incrementally decreasing in parallel for a progressively corrected footwear sole or orthotic 700, as viewed in a frontal plane cross section in an upright, unloaded condition.
Figure 7:
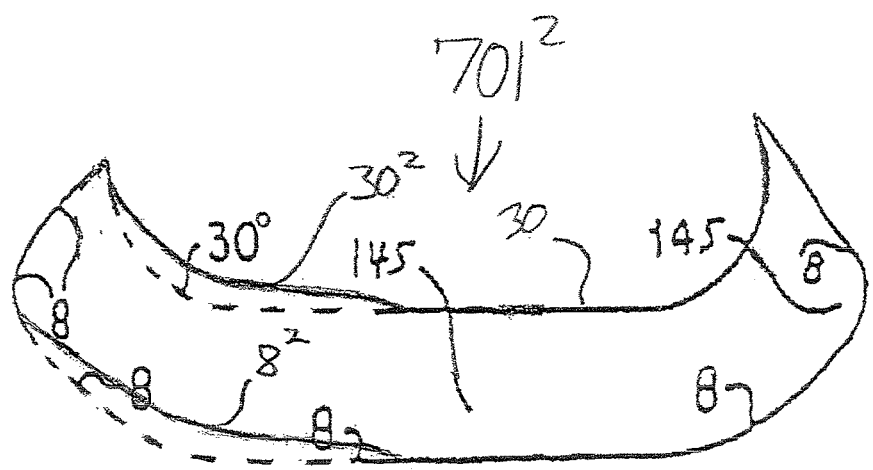
Figure 8:
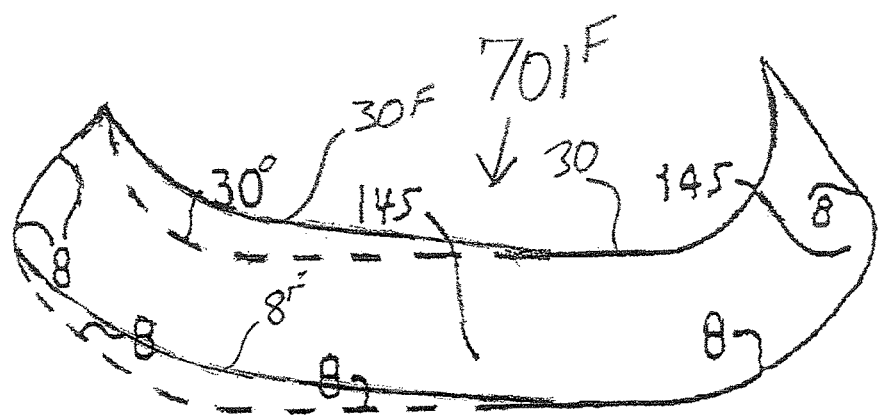

FIG. 3 shows the same figure as FIG. 2, but with an example of a new incremental corrective inner surface $30^1$, the progressively corrected footwear sole or orthotic 700, shown as $700^1$, therefore being thicker in the area of inner surface $30^1$. Alternatively, the incremental correction or corrective structure shown in inner surface $30^1$ could instead be made in outer surface 8 (as could subsequent corrections in FIGS. 4 and 5), as shown in FIGS. 6-8. Also, material density or firmness increases (like those shown in FIGS. 21-23 and 25 of the incorporated '665 application) in the sole or orthotic area adjacent to inner surface $30^1$ can produce a similar corrective effect. Decreases in thickness or material density or firmness (like those shown in FIGS. 27A-C, 28C-D and 28F of the incorporated '665 application) in the sole or orthotic can also be used for a corrective effect. Such progressive corrections can be made anywhere in or on the footwear sole or orthotic (or upper of either) or in combinations of both, including variations in frontal plane cross sections in different parts of the sole, such as the forefoot, heel, or midfoot portions (as shown in FIGS. 28A-F of the incorporated '665 application).

Figure 4:
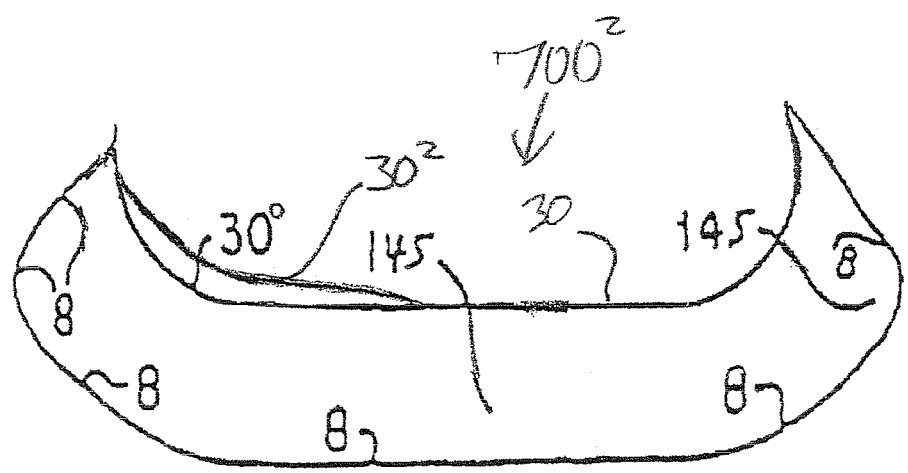

FIG. 4 shows the same figure as FIG. 3, but with another progressive example of an even thicker new incremental corrective inner surface $30^2$ for a progressively corrected footwear sole or orthotic 700, shown as $700^2$. Other thickness or material firmness or density correction increments are possible, as previously described in FIG. 3 above.

Figure 5:
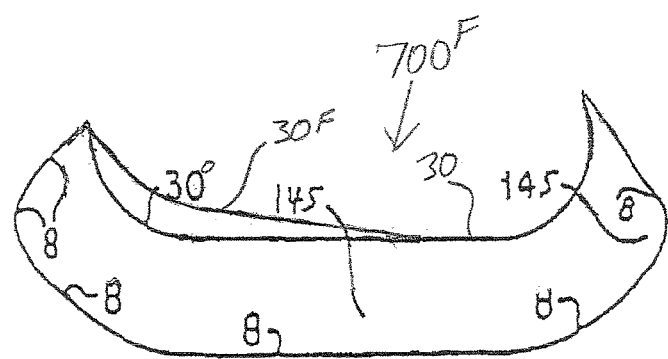

FIG. 5 shows the same figure as FIGS. 2-4, but with another progressive example of an even thicker final new incremental corrective inner surface $30^F$, for a progressively corrected footwear sole or orthotic 700, shown as $700^F$. Again, other thickness or material firmness or density correction increments are possible, as previously described in FIGS. 3 and 4 above.

Figure 11C:
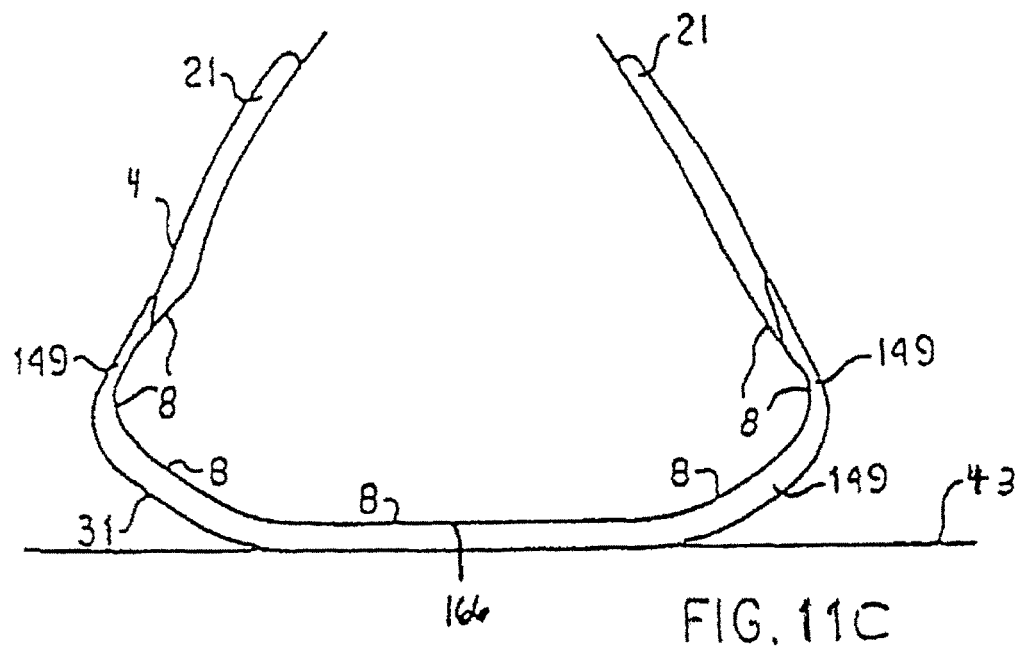

Although corrections in the form of thickness increases caused by changes in the inner surface 30 of the example removable midsole or orthotic insert 145 are shown above in FIGS. 3-5, similar corrections can be made in the outer surface 31 (shown in FIG. 11C and other figures of the incorporated '665 application) of the footwear sole or orthotic, including the bottom or sides. Such outer surface 31 corrections can be made independently or in combination with the inner surface 30 corrections described in FIGS. 3-5 above (and are shown combined in FIGS. 6-8 below). Other thickness or material firmness or density corrections can be used in outer surface 31 corrections, as previously described for inner surface 30 corrections in FIG. 3 above.

In summary, this embodiment of the invention includes a footwear sole or an orthotic or combinations of both including a set of incrementally different inserts forming a progressive sequence. The progressive sequence includes inserts having corrective structures that are incrementally closer to a final corrective structure than a corrective structure of a previous insert in the sequence. The corrective structure of the inserts may change in one or more of shape, thickness and firmness of at least one portion of the at least one insert as compared to the previous insert in the sequence. Each of the inserts of the set is worn for a period of time in order of the progressive sequence as part of the footwear sole and/or orthotic.

FIGS. 6-8 show the same figures as FIGS. 3-5, but with the outer surface 8 of the removable midsole or orthotic insert 145 shown modified in parallel (including curves) with the inner surface 30 corrections of FIGS. 3-5, so that the thickness of the progressively corrected footwear sole or orthotic 701, remains substantially the same (although the figures shown are somewhat approximate), while the shape only of the insert 145 is modified incrementally and progressively from FIG. 6 through FIG. 8, shown as $701^1$, $701^2$, and $701^F$, with outer surface 8 of the insert 145 changing from $8^O$ to $8^1$, then $8^2$, and finally $8^F$.

In summary, this embodiment of the invention includes a footwear sole or an orthotic or combinations of both, comprising a set of incrementally different inserts forming a progressive sequence. The progressive sequence includes at least one insert comprising a corrective structure that is incrementally closer to a final corrective structure than at least one previous insert in the sequence. The corrective structure of the at least one insert is provided by at least a change in shape of at least one portion of the at least one insert as compared to the previous insert in the sequence. Each of the inserts of the set is worn for a period of time in order of the progressive sequence as part of the footwear sole and/or orthotic.

FIGS. 9A-F show (in multiple frontal A-D, longitudinal E, and horizontal F plane cross sections) an example of the invention $701^O$ in the form of a removable midsole or orthotic insert $145^O$ (composed of midsole material 148, for example) with inner and outer surfaces that conform to the shape of a wearer's load-bearing foot sole (with both curved portions, for example under the wearer's main longitudinal arch, and flatten portions, for example under the wearer's heel). The outer or bottom sole 149 is shown with all of the middle portion flattened so that some portions are flattened where some portions of the adjacent insert 145 are curved; this is a example of an economically lower cost approach to incorporating a set of one or more incrementally different inserts 145 that are customized for the individual user that can be used with a non-customized, standard sized bottom sole and upper. Also, FIG. 9 shows an upper 21 that is integrated into the bottom sole 149 (and/or midsole 148) so that the bottom sole and upper can be made of the same material, such as a foamed plastic like classic Crocs™ or Waldies™ clogs.

In addition, FIGS. 9A-F show an example of an initial state or original removable midsole or orthotic insert $145^O$, while corresponding FIGS. 10A-F show an example of a final state of a removable midsole or orthotic insert $145^F$ wherein the corrected insert is fully rounded like a wearer's unloaded foot sole in a neutral, upright position. FIGS. 10A-F can include a bottom sole 149 and upper 21, as well as a heel lift, like FIGS. 9A-F (not shown separately).

FIG. 11A shows an example of the invention 701 as a sole 28 or insert 145 with an inner sole layer (and/or insole) including a combined pressure and thermally moldable material such that a wearer can at least partially or fully custom mold the inner surface 30 to the shape of the wearer's foot sole 27, in a manner similar to a Montrail™ CTX™ foam material used in a Molokai or Molokini model sandal.

FIGS. 11B-H are from the applicant's previously incorporated prior '665 application showing examples of the removable midsole or orthotic insert 145 in various FIG. 11B-11H embodiments, including a FIG. 11D perspective view of the incremental correction 700 invention with an insert 145 example with compartments 161 or the 510 or 511 or 513 invention. FIGS. 11G and 11H are FIGS. 11S and 11V of the incorporated '665 application.

Figure 12:
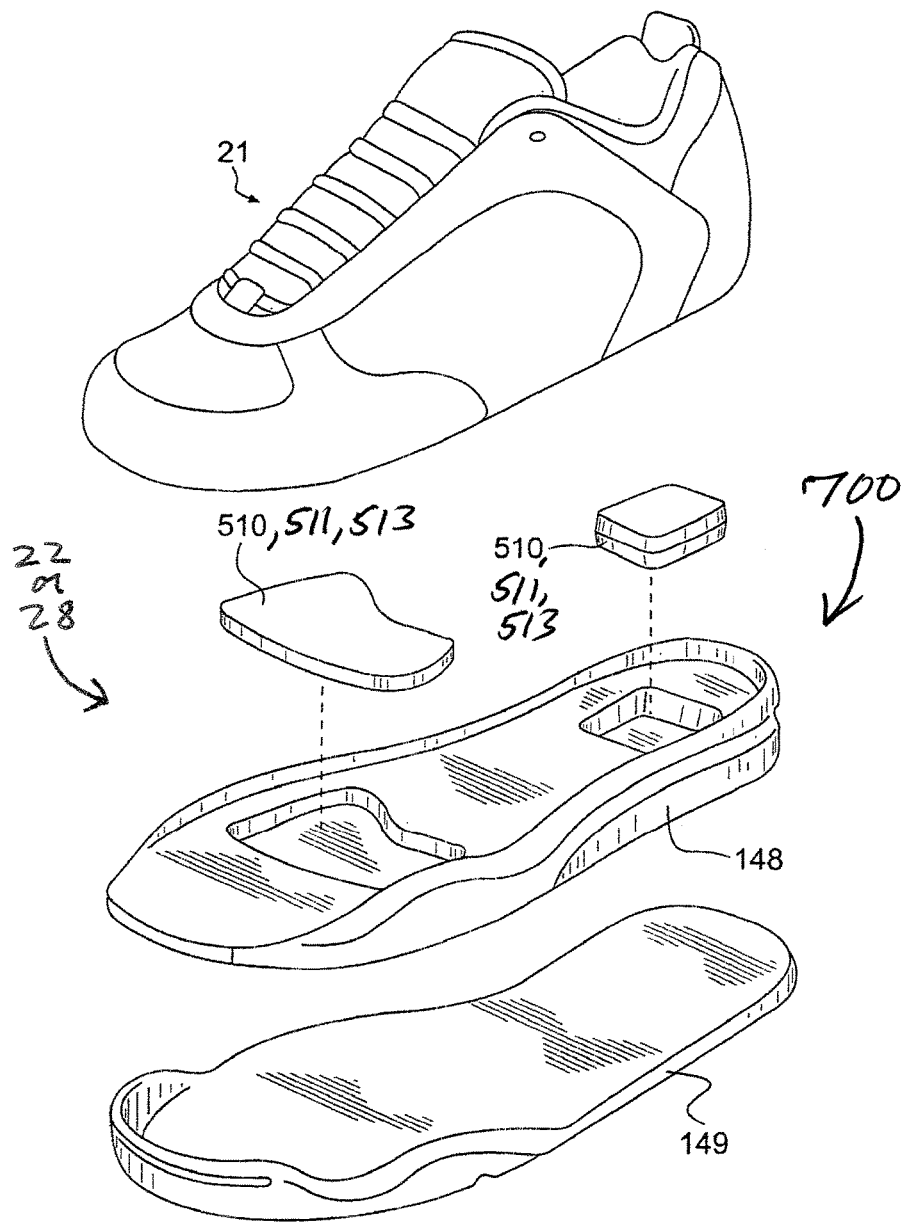
FIG. 12 shows FIG. 1C from the Ser. No. 11/802,930 application with an example of the incremental correction 700 invention and the applicant's 510 or 511 or 513 inventions.

FIG. 12 is FIG. 1C from the applicant's incorporated prior Ser. No. 11/802,930 application and shows the incremental correction 700 invention in a footwear sole 22 or 28 or orthotic with one or more of the applicant's 510 or 511 or 513 invention.

The above described examples can provide a typical excessively pronated foot (i.e. often called a "flat foot") with progressive correction to a more normal position with better defined longitudinal arches results in a corrected footwear sole or orthotic that better supports the foot's natural function by maintaining its natural shape, while deforming under body weight pressure as does the wearer's bare foot, providing a more natural energy return with each stride during locomotion.

Many of the typical foot problems known to podiatrics and/or orthopedics can be advantageously treated using the above described approaches employing progressively corrected sets of footwear soles and/or orthotics 700 or 701. To take but one simple example, a hammer toe deformity, either on a single foot or bilaterally, can be corrected in the manner described above, in which the normal arches (longitudinal and transverse) of the foot or feet are restored through gradual correction, during which process the position of the big toe is straightened from a bent in position to a more normal, straighter position.

Generally, the progressively corrected sets of footwear soles and/or orthotics 700 or 701 provide a way of correcting bilateral skeletal asymmetry in bipedal humans (and animals, including non-bipedal), including both right versus left foot and ankle asymmetry, but also all other bilateral asymmetries, including of the lower limbs and associated knee and hip joints, as well as the pelvis and lumbar spinal, and the rest of the spine, including the cervical spine, and all other associated upper body limbs and joints, including the skull, and associated muscles, ligaments, and tendons, and soft tissues, such as the viscera contained and supported by the pelvis, for example. The gradual correction provided by the progressively corrected soles or orthotics 700 or 701 allow for gradual bone reformation where the outset of gradual pain can be a guide to modifying or further slowing the correction, whereas imposing the entire correction at once is likely to result in significant pain and/or sudden joint injury of potentially serious nature, especially if the initial diagnosis or correction parameters prove to be incorrect and therefore in need of modification.

The gradual correction of the soles or orthotics 700 or 701 can include gradual modification of the amount of heel lift, such as gradual reduction, or gradual introduction of negative heel lift (i.e. forefoot lift). Similarly, any other footwear sole or orthotic corrections commonly used in orthopedics, podiatry, and related fields, including for example lateral wedges or posts, can be incrementally introduced.

Any example of a new invention of progressively corrected footwear soles and/or orthotics 700 or 701 shown in this application in the preceding FIGS. 1-11 and/or associated textual specification can be combined with any other part of any one or more other of the prior art or the applicant's prior invention examples shown in FIGS. 1-3, 5-7, 9, 11-42, 44-52, 55-62, 64-82 from prior published FIGS. 1-82 of the applicant's published application Ser. No. 11/282,665 previously incorporated by reference herein in its entirety, to make new and useful improvements over the existing art.

Such useful combinations include, but are not limited to, those combinations that include one or more features of FIGS. 1-11 and: incorporate uppers that envelope the midsole and/or outsole and/or other features shown in published application '665 prior FIGS. 5-7 and 13; incorporate anthropomorphic shapes and/or chambers and/or other features shown in prior FIGS. 9 and 10; incorporate integral or insertable orthotics or microprocessor-controlled variable pressure and/or other features shown in prior FIG. 11; incorporate sipes and/or other features shown in prior FIG. 12; use uniform thickness (measured in frontal plane cross-sections) in rounded sole side or sole bottom portions, especially at essential support and stability elements and/or other features shown in prior FIGS. 14-16, 29-46 and 76-77; use increased or decreased (or variable) thickness in rounded sole side portions and/or other features shown in prior FIGS. 17-20, 24, and 27-28; use increased or decreased density or firmness in rounded sole side or bottom portions and/or other features shown in prior FIGS. 21-23 and 25-26; use rounding of the outer surface of the midsole on a sole side and/or other features shown in prior FIG. 43A; employ bent-in rounded sides and/or other features shown in prior FIG. 47; uses bulges with or without uniform thickness, at important support or propulsion areas and/or features shown in prior FIGS. 48 and 75; incorporates a flat heel (meaning no heel lift) and/or other features shown in prior FIGS. 51A-51E; incorporates negative heel embodiments and/or other features shown in prior FIGS. 49A-49D and 50A-50E; use rounded sides with variable thickness and firmness and/or other features shown in prior FIG. 52; employs sipes and/or other features shown in prior FIGS. 53-57, 70-71 and 73; incorporates fiber and/or multiple layers of chambers and/or other features shown in prior FIGS. 58-60; employ shoe soles or orthotics with sufficient width throughout or at specific portions to support a wearer's bone structures throughout a full range of motion and/or other features shown in prior FIGS. 61-65 and 72; uses relatively planar sides with rounded underfoot sole portions and/or other features shown in prior FIGS. 66 and 67; uses similarly shaped rounding on sole sides of different thickness at different parts of the sole and/or other features shown in prior FIG. 69; uses a variation of heel or forefoot lifts and/or other features shown in FIG. 74; and/or other features shown in prior FIGS. 78-82.

In addition, any example of a new invention of progressively corrected footwear soles and/or orthotics 700 or 701 shown in this application in the preceding FIGS. 1-11 and/or associated textual specification can be combined with any other part of any one or more other of the prior art or the applicant's prior invention examples shown in prior published FIGS. 83-127 of the applicant's published application Ser. No. 11/282,665 previously incorporated by reference herein in its entirety, especially including the applicant's 510 or 511 or 513 inventions shown in FIGS. 83-114 of the '665 application, to make new and useful improvements over the existing art.

Such useful combinations include, but are not limited to, those combinations that include one or more features of FIGS. 1-11 and incorporate: one or more siped compartments, chambers, or bladders inserts 510 as shown generally in FIGS. 83-88, and in specific footwear or orthotic examples in FIGS. 89-96, including with computer-control in FIG. 97 and magnetic fluid in FIGS. 98-99; inserts 511 including also sipes shown generally in FIG. 100; unitary sipe or slit inserts 513 shown generally in FIG. 101-103; inserts 510 included in footwear uppers in FIGS. 104 and 105; inserts 510 and 513 in helmet examples in FIG. 106; inserts 510 incorporating midsole foamed materials in examples in FIGS. 107 and 108; insert 510 in a footwear sole or orthotic shank example; insert 510 in a ball example in FIG. 109, a tire example in FIG. 110, a human breast implant example in FIG. 111, a structural or support element in FIG. 112, a golf club example in FIG. 113, and a spinal disk example in FIG. 114, as well as many other examples described in paragraphs 0534, 0535, and 0536.

Furthermore, any example of a new invention of progressively corrected footwear soles and/or orthotics 700 or 701 shown in this application in the preceding FIGS. 1-11, and/or associated textual specification can be combined with any other part of any one or more other of the prior art or the applicant's prior invention examples shown in FIGS. 1-87 of the applicant's U.S. patent application Ser. No. 11/802,033, published on Apr. 10, 2008 as Pub. No. 2008/0083140 A1 which is incorporated by reference herein in its entirety, especially including the applicant's 510 or 511 or 513 inventions shown in FIGS. 45-87 of the '930 application, to make new and useful improvements over the existing art.

In addition, any example of a new invention of progressively corrected footwear soles and/or orthotics 700 or 701 shown in this application in the preceding FIGS. 1-11, and/or associated textual specification can be combined with any other part of any one or more other of the prior art or the applicant's prior invention examples shown in FIGS. 1-87 of the applicant's patent application Ser. No. 11/802,930, published on Apr. 17, 2008 as Pub. No. US 2008/0086916 A1, which is incorporated by reference herein in its entirety, especially including the applicant's 510 or 511 or 513 inventions shown in FIGS. 45-87 of the '930 application, to make new and useful improvements over the existing art.

FIGS. 13A-14B show the applicant's new inventions incorporating new forms of devices with one or more internal (or mostly internal) sipes, including slits or channels or grooves and other shape, including geometrically regular or non-regular shapes, such as anthropomorphic shapes, into a large variety of products, including footwear and orthotics, athletic, occupational and medical equipment and apparel, padding for equipment and furniture, balls, tires and any other structural or support elements in a mechanical, architectural or any other device.

FIGS. 13A-20 show, as numeral 510, examples of a device or flexible insert including siped compartments 161 or chambers 188 or bladders (another term used in the art) for use in any footwear soles, including conventional soles 22 or the applicant's prior inventions, including footwear/shoe soles 28 and midsole inserts 145, or for orthotics 145 as described in the applicant's WO 02/09547 WIPO publication, including for uppers for footwear or orthotics (or including uppers), or for other flexibility uses in athletic equipment like helmets and apparel including protective padding and guards, as well as medical protective equipment and apparel, and other uses, such as protective flooring, improved furniture cushioning, balls and tires for wheels, and other uses.

The device or flexible insert with siped compartments or chambers 510 include embodiments like two or more of either compartments 161 or chambers 188 or bladders (or a any mix including two or more of a compartment, a chamber, and a bladder) that are separated at least in part or in several parts or mostly or fully by an internal sipe 505. The flexible insert 510 can be inserted during assembly of an article by a maker or manufacturer or is insertable by a user or wearer (into an article like a shoe, for example, as part of a removable midsole insert 145 described above), or integrated into the construction of a device as one or more components.

Siped compartments or chambers 510 include example embodiments such as FIGS. 13A-20 which generally show at least one inner compartment 161 or chamber 188 inside at least one other outer compartment 161 or chamber 161; and the two compartments/chambers 161/188 being separated by an internal sipe 505.

One practical example embodiment of the invention is any prior commercial embodiment of Nike Air™ gas bladder or compartment (like typical examples in FIGS. 12-16 of U.S. Pat. No. 6,846,534, which is hereby incorporated by reference) that is installed unattached, as is, located within the space enclosed partially or fully by a new, slightly larger outer compartment of one additional layer of the same or similar material, with the same or a simpler or the simplest geometric shape; that is, not necessarily following indentations or reverse curves, but rather incorporating straighter or the straightest lines, as seen in cross-section: for example, following the outermost side curvature seen in FIGS. 12-16, but with upper and lower surfaces that are substantially flat and parallel (or curved and parallel), to facilitate ease of movement between the two surfaces of the sipe 505 formed, increasing the resulting flexibility.

The new additional, outer compartment thus thereby has created by its presence an internal sipe 505 between the two unconnected compartments. The new internal sipe 505 provides much greater flexibility to any footwear sole 22 or 28, since it allows an inner, otherwise relatively rigid Nike Air™ compartment structure to become an inner compartment 501 (instead of typically being fixed into the other materials such as EVA of the footwear sole) to move freely inside the new outer compartment 500, which becomes a new compartment that is fixed to the footwear sole, rather that the conventional Nike Air™ bladder. The flexibility improvement allows the shoe sole to deform under a body weight load like a wearer's bare foot sole, so that stability is improved also, especially lateral stability.

The result is that the conventional, inner Nike Air™ compartment now contained by a new outer compartment can move easily within the overall footwear sole, allowing the sole to bend or flex more easily in parallel with the wearer's bare foot sole to deform to flatten under a body weight load, including during locomotion or standing, so that footwear sole stability is improved also, especially lateral stability. The extent to which the inner Nike Air™ compartment is "free-floating" within the new outer compartment can be controlled or tuned, for example, by one or more attachments (permanent or adjustable) to the outer compartment or by the media in the internal sipe.

The internal sipe 505 includes at least two surfaces that can move relative to each other to provide a flexibility increase for a footwear sole so that the shape of the footwear sole can deform under a body weight load to better parallel to the shape of the barefoot sole of a wearer under a same body weight load. The relative motion between the two internal sipe 505 surfaces increases the capability of the footwear sole to bend during locomotion under a wearer's body weight load to better parallel the shape of said wearer's bare foot sole.

In an analogous way, especially to the thicker heel portion of a typical shoe sole, a thick urban area telephone book has in effect hundreds of "internal sipes", each page being in effect separated by a sipe from each adjacent page, each of which thereby is able to move freely relative to each other, resulting in a flexible telephone book that bends quite easily. In contrast, if the same wood fiber material with the same dimensions as a thick telephone book were formed instead into a single piece with no pages, like a solid particle board, it would be quite rigid. Also, the sliding motion between internal support surfaces within the shoe sole 28 allowed by internal sipe 505 in response to torsional or shear forces between a wearer's foot and the ground assists in controlling and absorbing the impact of those forces, whether sudden and excessive or chronically repetitive, thereby helping to protect the wearer's joints from acute or chronic injury, especially to the ankles, knees, hips, lower back, and spine.

A benefit of the siped compartments/chambers 510 is that, as a single unitary component, it can be used in a conventional manner in constructing the footwear sole 28, generally like that used with a conventional single layer compartment such as used in Nike Air™; i.e. the outer surface of 510 can, as a useful embodiment, adhere to the adjacent materials like plastic such as PU (polyurethane) or EVA (ethyl vinyl acetate) or rubber of the footwear sole that contact the 510 component, just as would be the case with the outer surface of existing single compartment 161 or chamber 188 of commercial examples of Nike Air™. However, the internal sipe 505 formed by the use of an inner compartment/chamber 501 in the siped compartment/chamber 510 provides flexibility in a footwear sole 28 that is absent in the relatively rigid footwear sole 28 formed with a conventional, single layer compartment 161 or chamber 188 of the many Nike Air™ commercial examples.

The sipe surfaces can in one useful example embodiment be formed by the inner surface (or part or parts of it) of the outer compartment 500 and the outer surface (or part or parts of it) of the inner compartment 501. Such sipe surfaces can be substantially parallel and directly contact each other in one useful embodiment example, but the two surfaces are generally not attached to each other, so that the sipe surfaces can move relative to each other to facilitate a sliding motion between the two surfaces.

The sipe surfaces can be in other useful forms that allow portions of the surfaces to be proximate to each other in an unloaded condition, rather than contacting; such surfaces can make partial or full direct contact under a wearer's body weight load (which can vary from a fraction of a "g" to multiple "g" forces during locomotion) or remain somewhat separated; the amount of sipe surface area making direct contact can also vary with a wearer's body weight load. The sipes surfaces also may not be parallel or only partially parallel, such as the areas of direct surface contact or proximal surface contact.

To preclude the surfaces of the internal sipe 505 from directly contacting each other (whether loaded or unloaded), the sipe surfaces can include an internal sipe media 506 located between the surfaces to reduce friction by lubrication and increase relative motion and therefore flexibility. Useful example embodiments of the internal sipe media 506 include any useful material known in the art (or equivalent), such as a liquid like silicone as one example, a dry material like Teflon™ as another example, or a gas like that used in Nike Air™ as a further example. The media 506 can be located in all of the sipe 505 or only part or parts, as shown in FIGS. 13A-14B.

The media 506 can be used to decrease (or increase) sliding resistance between the inner surfaces of the sipe; for example, to lubricate with any suitable material known in the art. The internal sipe media 506 is an optional feature.

The siped compartments/chambers 510 can be located anywhere in the footwear sole or orthotic or upper and can be used in other applications, including non-footwear applications where flexibility increases are useful). The siped compartments/chambers 510 can be made, for example, with any methods and materials common in the footwear arts or similar arts or equivalents, like those in various Nike Air™; see for example U.S. Pat. Nos. 4,183,156 and 4,219,945 to Rudy (which show fluid-filled bladder manufacturing through a flat sheet bonding technique), U.S. Pat. No. 5,353,459 to Potter et al. (which shows fluid-filled bladders manufactured through a blow-molding process), as well as U.S. Pat. No. 6,837,951 and FIGS. 12-16 of U.S. Pat. No. 6,846,534, all of which patents are hereby incorporated by reference) or similar commercial examples like Reebok DMX™ compartments in its original form, as seen for example U.S. Pat. No. 6,845,573 (hereby incorporated by reference), column 5, line 41 to column 6, line 9), or New Balance N-ergy™ (see for example FIG. 1 of WIPO Pub. No. WO 00/70981 A1, but note that, as a example, at least the initial production versions of the N-erny compartment should have less rigidity to allow desirable flexibility) or Asics Gel™ (many versions) compartments or future equivalents of any, or with less common materials, such as fibers described above incorporated into or on the surface of the material of the siped compartment/chambers 510, including either elastic fibers or inelastic fibers or a mix. The siped compartment/chambers 510 can be of any practical number in a footwear sole or any shape, of which useful example embodiments include regular geometric shapes or irregular shapes, including anthropomorphic shapes; and the 510 number or shape can be symmetrical or asymmetrical, including between right and left footwear soles.

Figure 13A:
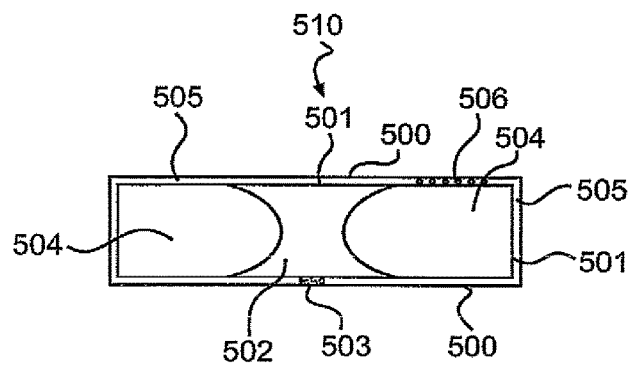
FIG. 13A shows a frontal or sagittal plane cross section view of an example of a device 510 such as a flexible insert with a siped compartment or chamber or bladder.

Either of the compartments 161 or chambers 188 of the siped compartment/chambers 510 can include one or more structural elements 502 like those common in the footwear art such as in Nike Air™ as noted in the above cited Rudy and Nike patents, also including Tuned Air™ (See for example U.S. Pat. No. 5,976,451 to Skaja et al, which is hereby incorporated by reference and which shows manufacturing of fluid-filled bladders through a vacuum-forming process) or Zoom Air™ (See for example FIGS. 1-3 of U.S. App. No. 2005/0039346 A1, which is hereby incorporated by reference); an example embodiment of inner compartments 501 with structural elements 502 is shown in FIG. 13A. The structural elements 502 can be made of any useful material known in the art and constructed in any manner known in the art.

FIGS. 107A and 108A of US 2006/0248749 show similar example embodiments wherein the structural elements 502 of the inner compartment 501 are formed with a specific shape and foamed plastic material such as PU or EVA like that of Nike Shox™ (See U.S. Pat. Nos. 5,353,523, 5,343, 639, and 6,851,204, which are hereby incorporated by reference) and Nike Impax™ (U.S. Pat. No. 500,585 S, which is hereby incorporated by reference), respectively, and can be affixed to the inner compartment 501, which can be reinforced as necessary (instead of to rigid lower and/or upper plates); the lower surface of the outer compartment 500 can be attached to an outer sole, at least in part or an outer sole can be integrated into the outer compartment 500 by thickening, for example, or incorporating rubber or rubber substitute material. Other commercial existing examples that can be similarly modified as a device or flexible insert or component 510 are Adidas a³™ Energy-Management Technology and Adidas™ Ground Control System (GPS)™, and Reebok DMX™ Shear Heel or other cushioning technologies.

Also, as shown in the example embodiments of FIGS. 108B and 107B of US 2006/0248749, since foamed plastic material does not require containment (unlike a gas, liquid, or most gels), if the structural elements 502 are sufficiently interconnected, like for example Nike Impax™ in FIG. 108B of US 2006/0248749, or if the separate support columns 32 and midsole wedge 40 of Nike Shox™ are modified to interconnect like the example shown in FIG. 107B of US 2006/0248749, then those connected structural elements 502 can form an integral inner compartment 501, the outer surface of which can form an internal sipe 505 with the new outer compartment 500. The interconnection can be complete, with each structural elements 502 connected to at least the closest other elements 502, as shown, or mostly complete, or partial. The Shox™ support columns 32 can be any practical number, such as existing examples of four or five or six (both commercially available) or more in the heel and many more in the forefoot of the shoe sole 22 or 28, for a total of eleven in existing commercial examples.

Figure 14A:
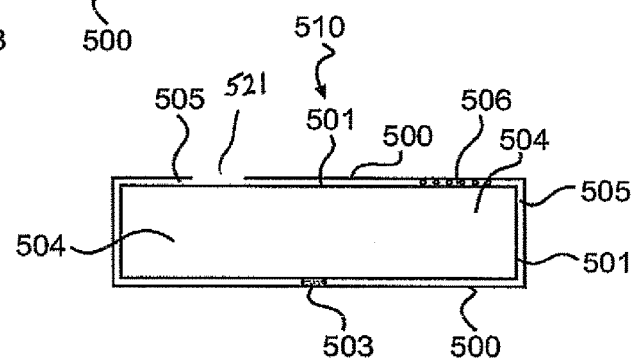
FIG. 14A shows a frontal or sagittal plane cross section view of an example of a device 510 such as a flexible insert with a siped compartment or chamber or bladder.
Figure 13B:
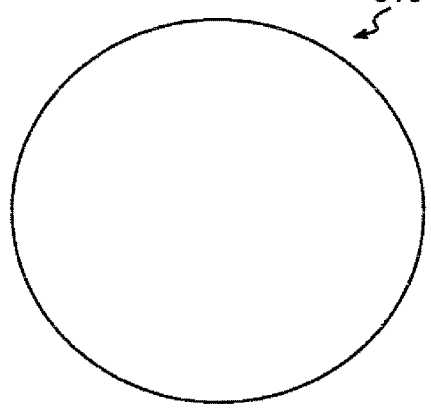
FIG. 13B shows a horizontal plane view of a device 510 example.
Figure 14B:
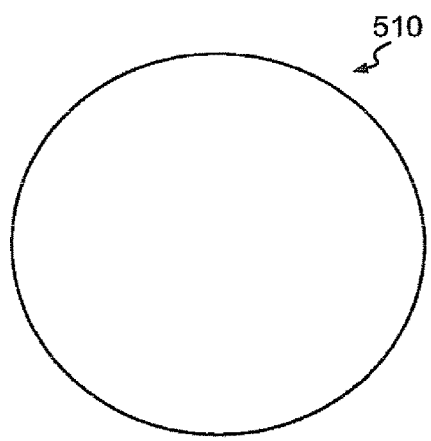
FIG. 14B shows a horizontal plane view of a device 510 example.
Figure 16:
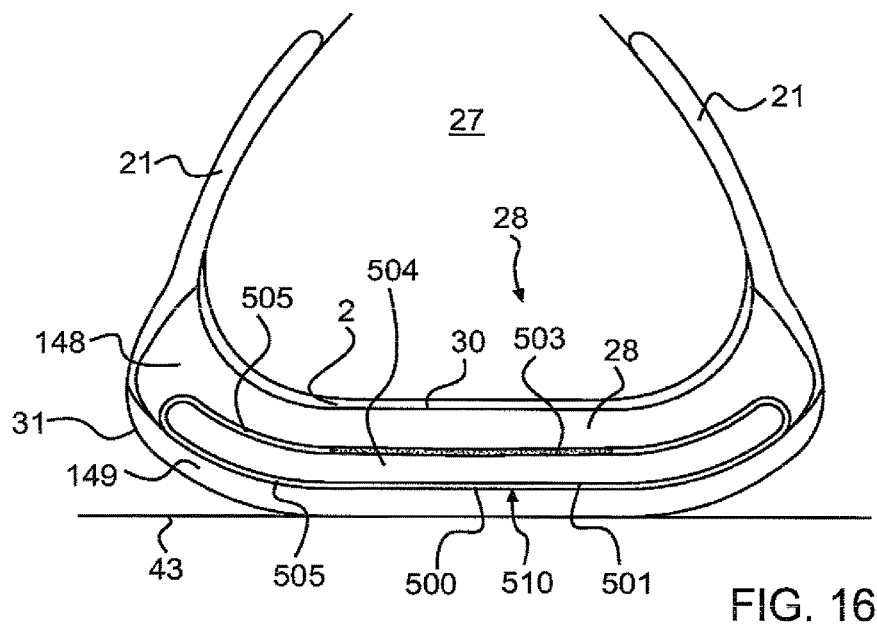
FIG. 16 shows a similar embodiment and view to that shown in FIG. 15, including also an attachment 503 between 500 and 501.

Any of the compartments or chambers 161/188 of the siped compartment 510 can be permanently or temporarily attached one to another with at least one attachment 503 of any useful shape or size or number or position; embodiment examples are shown in FIGS. 13A, 14A, and 16. Anthropomorphic designs would include positioning attachments 503 on the internal sipe 505 closest to a wearer's foot sole, so that the remaining sipes 505 would have a U shape in cross-section, like the structure of human foot sole fat pads, which are analogous to the cushioning midsole and midsole components of footwear soles.

The attachments 503 can be simply passive (i.e. static) or actively controlled by electronic, mechanical, electromagnetic, or other useful means. The attachments 503 can, for example, be designed to break away as a failsafe feature to compensate for a predetermined extreme torsional load, for example, to reduce extreme stress on critical joints (in lieu of a wearer's cartilage, tendons, muscle, bone, or other body parts being damaged); the attachments 503 can then be reset or replaced (or, alternatively, return automatically to a normal position). Example embodiments of the compartments and chambers 500/501 can include a media 504 such as a gas (like that used in Nike Air™ or ambient atmospheric air), a liquid or fluid, a gel, a foam (made of a plastic like PU or EVA, both of which are common in the footwear art, or equivalent, or of a rubber (natural or synthetic) or blown rubber or a rubber compound or equivalent or of another useful material or of a combination of two or more of the preceding foam plastic/rubber/etc.) or a useful combination of one or more gas, liquid, gel, foam, or other useful material.

Also, any inventive combination that is not explicitly described above in the example shown in FIGS. 13A-13B is implicit in the overall invention of this application and, consequently, any part of the example embodiments shown in preceding FIGS. 13A-13B and/or associated textual specification can be combined with any other part of any one or more other elements of the invention examples described in FIGS. 84-114 and/or associated textual specification of US 2006/0248749 and/or, in addition, can be combined with any one or more other elements of the inventive examples shown in FIGS. 1-82 & 115-117 and/or associated textual specification of US 2006/0248749 to make new and useful improvements over the existing art.

FIG. 14A shows an example of an embodiment of siped compartment/chambers 510 wherein either the inner compartment/chamber 501 or the outer compartment 500 can have one or more openings, for pressure equalization, assembly facilitation, or other purposes. Also, any inventive combination that is not explicitly described above in the example shown in FIGS. 14A-14B is implicit in the overall invention of this application and, consequently, any part of the example embodiments shown in FIGS. 14A-14B and/or associated textual specification can be combined with any other part of any one or more other elements of the invention examples described in FIGS. 83 and 87-114 and/or associated textual specification of US 2006/0248749 and/or, in addition, can be combined with any one or more other elements of the inventive examples shown in earlier FIGS. 1-82 & 115-117 and/or associated textual specification of US 2006/0248749 to make new and useful improvements over the existing art.

FIGS. 15-20 show, in frontal plane cross sections in the heel area, example footwear embodiments with siped compartment/chambers 510 located in footwear soles 28, which are shown with curved sides but which sides can also be planar in another embodiment; or which is shown with flattened inner and outer surfaces underneath the wearer's foot sole but which can be curved in a different embodiment.

Figure 15:
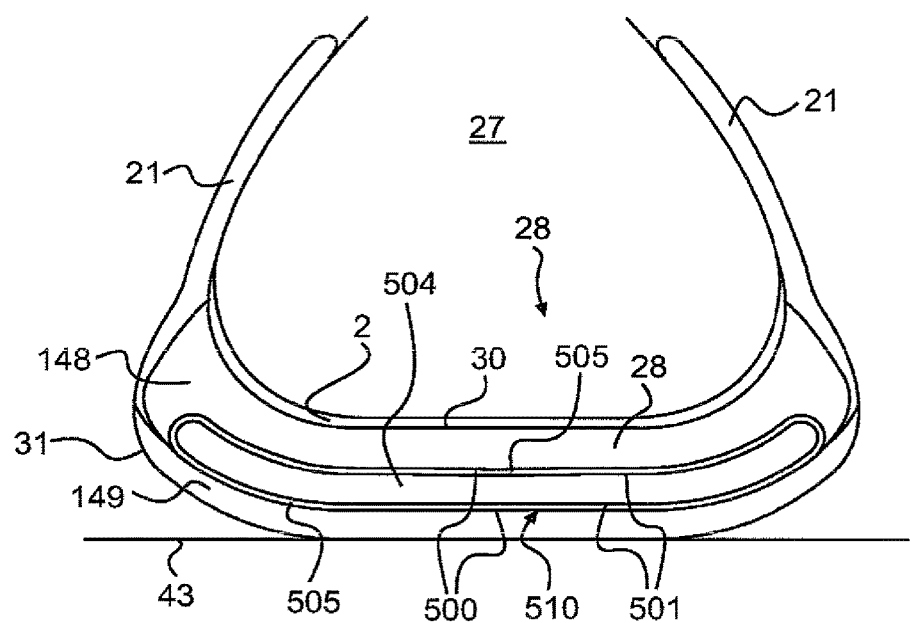
FIG. 15 shows, in a frontal plane cross section in the heel area, a shoe and shoe sole including a single siped compartment 510.

FIG. 15 shows an example embodiment with single outer compartment 500 and a single inner compartment/chamber 501.

FIG. 16 shows a similar example embodiment with an attachment 503 between 500 and 501.

Figure 17:
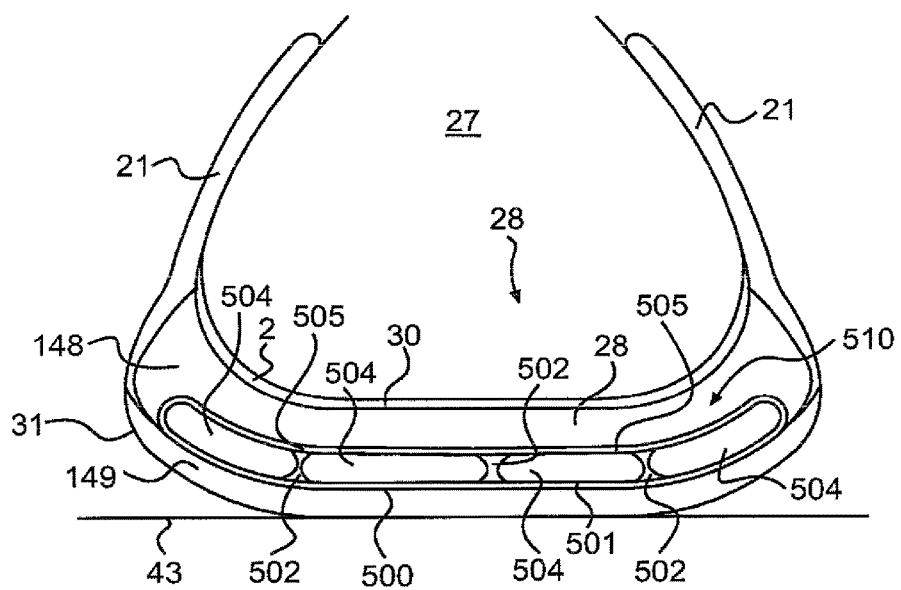
FIG. 17 shows a similar embodiment and view to that shown in FIG. 15, including also an inner compartment/chamber 501 with a number of inner compartment structural elements 502.

FIG. 17 is a similar example embodiment to that shown in FIG. 15 and includes also an inner compartment/chamber 501 with a number of structural elements 502.

Figure 18:
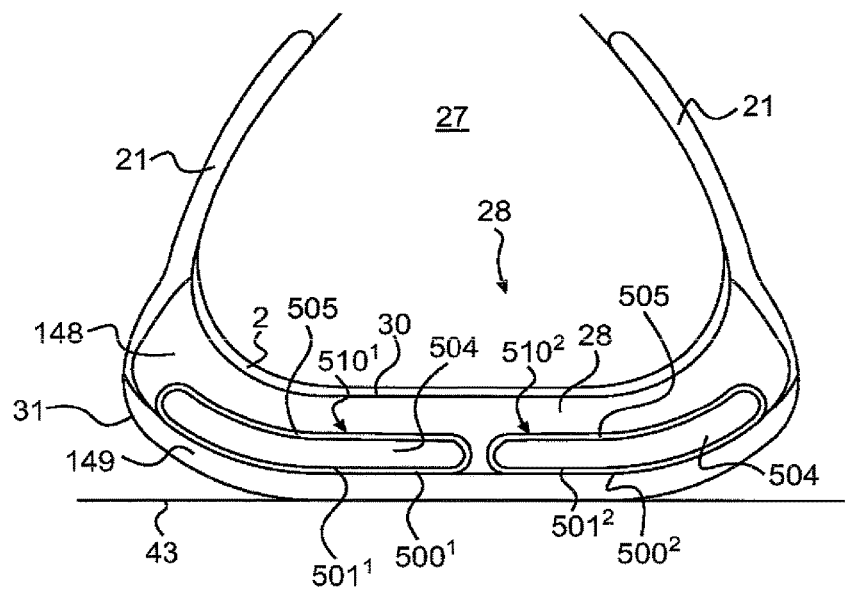
FIG. 18 shows a similar embodiment and view to that shown in FIG. 15, including also more than one siped compartment 510.

FIG. 18 shows an example embodiment with more than one siped compartment/chambers 510, including outer compartment/chambers 500, each with an inner compartment/chamber 501; not shown is another example embodiment with more than one inner compartments/chambers 501 in each of more than one outer compartment/chamber 500, another among many useful variations.

Also, any inventive combination that is not explicitly described above in the examples shown in FIGS. 16-18 is implicit in the overall invention of this application and, consequently, any part of the example embodiments shown in FIGS. 16-18 and/or associated textual specification can be combined with any other part of any one or more other elements of the invention examples described in FIGS. 83-89 and 93-114 and/or associated textual specification of US 2006/0248749 and/or, in addition, can be combined with any one or more other elements of the inventive examples shown in FIGS. 1-82 & 115-117 and/or associated textual specification of US 2006/0248749 to make new and useful improvements over the existing art.

Figure 19:
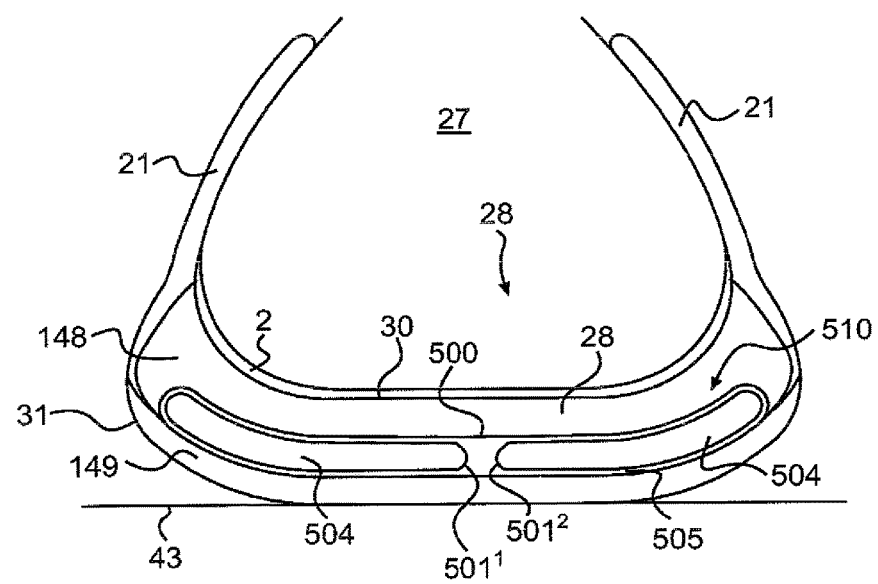
FIGS. 19 and 20 show a similar embodiment and view to that shown in FIG. 15, including also more than one inner compartments 501 in an outer compartment 500.
Figure 20:
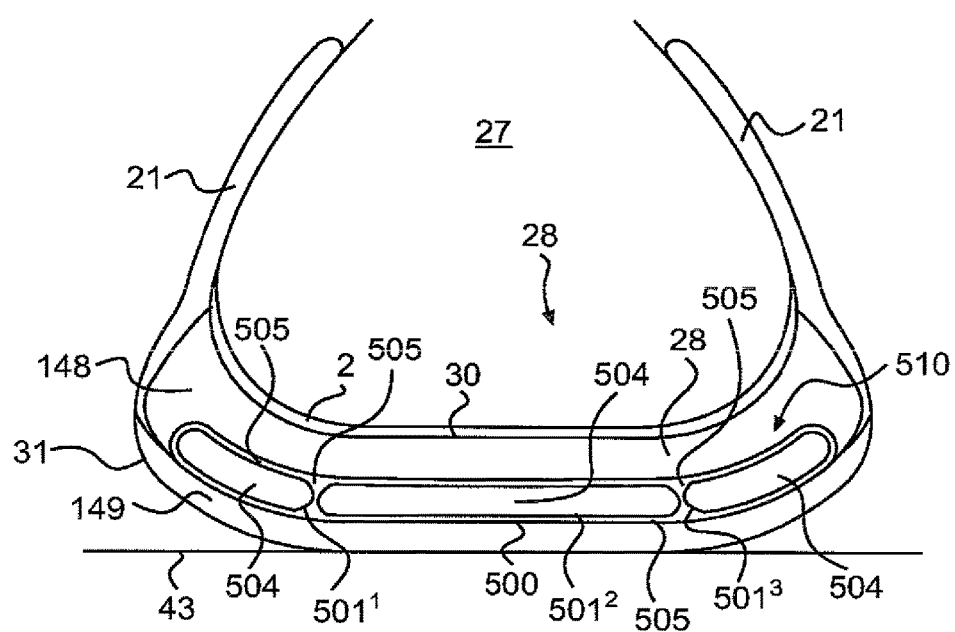

FIG. 19 shows a similar example embodiment to FIG. 15 and including a number of inner compartments 501 within a single outer compartment/chamber 500, as does FIG. 20. Any practical number of inner compartments 501 can be a useful embodiment of the general invention.

Also, any inventive combination that is not explicitly described above in the examples shown in FIGS. 15 and 19-20 is implicit in the overall invention of this application and, consequently, any part of the example embodiments shown in preceding FIGS. 15 and 19-20 and/or associated textual specification can be combined with any other part of any one or more other elements of the invention examples described in FIGS. 83-88, 90-92, and 95-114 and/or associated textual specification of US 2006/0248749 and/or, in addition, can be combined with any one or more other elements of the inventive examples shown in earlier FIGS. 1-82 & 115-117 and/or associated textual specification of US 2006/0248749 to make new and useful improvements over the existing art.

Figure 21A:
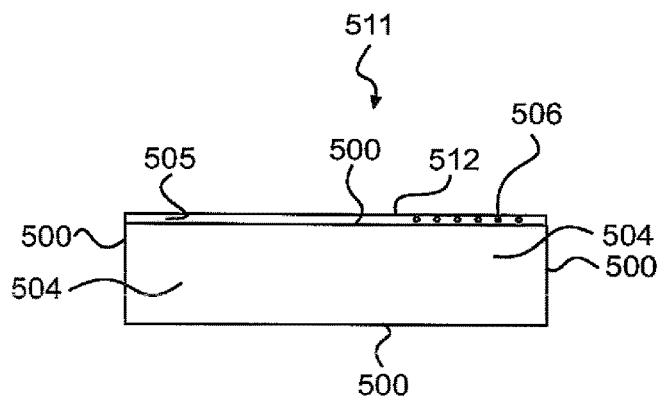
FIG. 21A shows, in a frontal or sagittal plane cross section, a flexible insert or component 511 including a singe compartment/chamber 161/188 or bladder with an associated internal sipe 505 component.
Figure 21B:
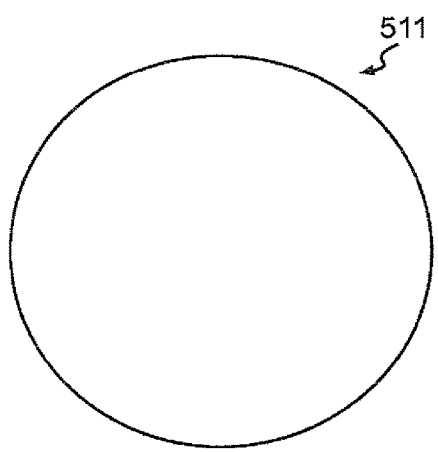
FIG. 21B shows a horizontal plane view of 511.

FIG. 21A shows an example embodiment of a flexible insert or component 511 including a single compartment/chamber 161/188 or bladder with an associated internal sipe 505 component, again for any footwear sole, including conventional 22, or other flexibility uses (such as those described above relative to insert 510), to form a single unitary siped compartment or chamber; the sipe 505 can extend to part or all of one side of the single compartment 500, as shown, or the sipe 505 can extend around portions of the other sides of the single compartment 500; FIG. 21B shows an example embodiment in a horizontal plane view of 511. The flexible insert 511 can be inserted during assembly of an article by a maker or manufacturer or is insertable by a user or wearer (into an article like a shoe, for example, as part of a removable midsole insert described above), or integrated into the construction of an article as one or more components.

A benefit of the single siped compartment/chamber 511 is that, as a single unitary component like 510, it can be used in a conventional manner in constructing the footwear sole 28, like that used with a conventional single layer compartment in Nike Air™; i.e. the outer surface of 511 can, as a useful embodiment, adhere to the adjacent material of the footwear sole that contact the 511 component, just as would the outer surface of a single compartment 161 or chamber 188. However, the internal sipe 505 component of the siped compartment/chamber 511 provides flexibility in a footwear sole 28 that is absent in the relatively rigid footwear sole 28 formed with a conventional, single layer compartment 161 or chamber 188.

The siped compartments/chamber 511 can be located anywhere in the footwear sole (and can be used in other, non-footwear applications where flexibility increases are useful). The siped compartments/chambers 511 can be made with any materials common in the footwear art, like those in various Nike Air™ commercial examples, or future equivalents, or with less common materials, such as fibers described earlier, including either elastic fibers or inelastic fibers or a mix. The siped compartment/chambers 511 can be of any practical number in a footwear sole, or any shape, of which useful embodiments include regular geometric shapes or irregular shapes, including anthropomorphic shapes; and the number or shape can be symmetrical or asymmetrical, including between right and left footwear soles.

Also, any inventive combination that is not explicitly described above in the example shown in FIGS. 21A-21B is implicit in the overall invention of this application and, consequently, any part of the example embodiments shown in preceding FIGS. 21A-21B and/or associated textual specification can be combined with any other part of any one or more other elements of the invention examples described in FIGS. 83-99 and 101-114 and/or associated textual specification of US 2006/0248749 and/or, in addition, can be combined with any one or more other elements of the inventive examples shown in FIGS. 1-82 & 115-117 and/or associated textual specification of US 2006/0248749 to make new and useful improvements over the existing art.

Figure 22A:
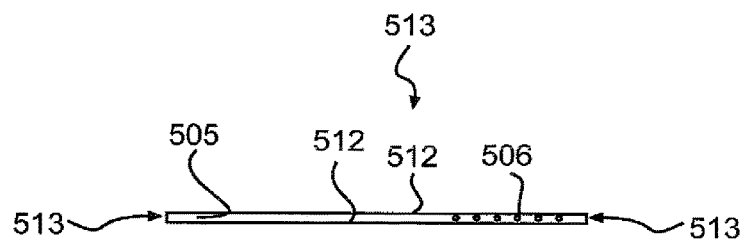
FIG. 22A shows, in frontal or sagittal plane cross section, a flexible insert or component 513 forming a unitary internal sipe.
Figure 22B:
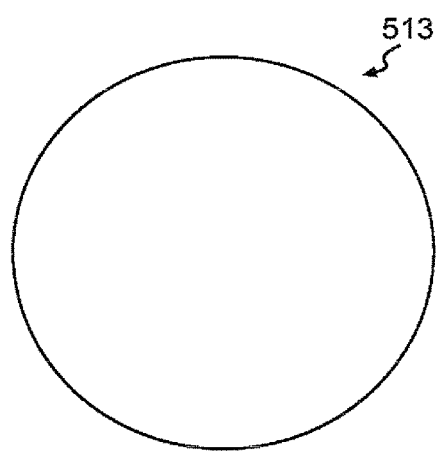
FIG. 22B is a horizontal plane view of 513.

FIG. 22A shows an example embodiment of a flexible insert or component 513 forming a unitary internal sipe for any footwear sole or orthotic or upper, including conventional sole 22, or other flexibility uses (such as those described above relative to insert 510), the embodiment shown employing a single internal flexibility sipe 505; FIG. 22B shows an example embodiment in a horizontal plane view of FIGS. 22A, 23A, and 24A. Multiple unitary internal sipes 513 can be used independently or synergistically anywhere in a footwear sole in other useful embodiments not shown; the sipes 513 can be stacked proximate to one another or apart, as viewed in a frontal or sagittal plane, for example; or the sipes 513 can overlap, as viewed in a horizontal plane, for example. The flexible insert 513 can be inserted during assembly of an article by a maker or manufacturer or is insertable by a user or wearer (into an article like a shoe, for example, as part of a removable midsole insert described above), or integrated into the construction of an article as one or more components.

In one useful example embodiment, the unitary internal sipe 513 can be made as a separate sole component like an extremely thin conventional gas compartment similar to a Nike Air™ compartment, but without the typical internal compartment structures (which in another useful embodiment can be present in some form if unattached to at least one inner surface so that relative motion between inner surfaces can occur to provide increased flexibility).

A benefit of the unitary internal sipe 513 is that, as a single unitary component like 510 and 511, it can be used in a conventional manner in constructing the footwear sole 28, roughly like that used with a conventional single layer compartment in Nike Air™; i.e. the outer surface of 513 can, as a useful embodiment, adhere to the other portions of the footwear sole that contact the 513 component, just as would the outer surface of a single compartment 161 or chamber 188. The unitary internal sipe 513 can be located as a separate component anywhere in the footwear sole (and can be used in other applications, including non-footwear applications where flexibility increases are useful). The unitary internal sipe 513 can be made with any materials common in the footwear art, like those in various Nike Air™ commercial examples, or future equivalents, or with less common materials, such as fibers described earlier, including either elastic fibers or inelastic fibers or a mix. The unitary internal sipe 513 can be of any practical number in a footwear sole, or any shape, of which useful example embodiments include regular geometric shapes or irregular shapes, including anthropomorphic shapes; and the number or shape can be symmetrical or asymmetrical, including between right and left footwear soles.

Figure 23A:
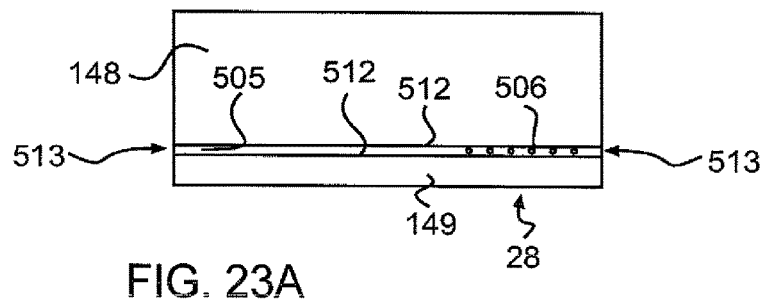
FIG. 23A shows, in frontal or sagittal plane cross section, the FIG. 22A embodiment of a unitary internal sipe 513 position as a separate component in a footwear sole.
Figure 24A:
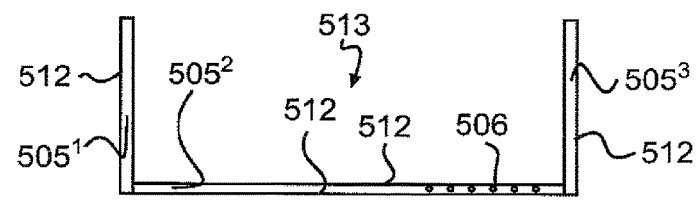
FIG. 24A shows, in frontal or sagittal plane cross section, the unitary internal sipe 513 in an embodiment including three separate internal flexibility sipes 505.
Figure 23B:
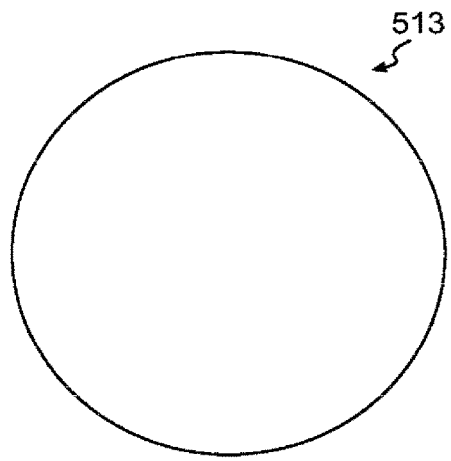
FIG. 23B is like FIG. 23B.
Figure 24B:
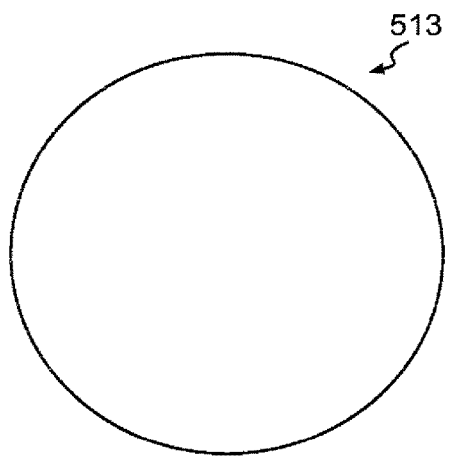
FIG. 24B is like FIG. 23B.

FIG. 23A shows the FIG. 221A example embodiment of a unitary internal sipe 513 positioned as a separate component in an embodiment of a footwear sole 28; alternatively, in another example embodiment not shown, the unitary internal sipe 513 can be completely enclosed in conventional midsole material like PU or EVA or similar material.

The applicant's other footwear U.S. Pat. Nos. 4,989,349; 5,317,819; 5,544,429; 5,909,948; 6,115,941; 6,115,945; 6,163,982; 6,308,439; 6,314,662; 6,295,744; 6,360,453; 6,487,795; 6,584,706; 6,591,519; 6,609,312; 6,629,376; 6,662,470; 6,675,498; 6,675,499; 6,708,424; 6,729,046; 6,748,674; 6,763,616; 6,789,331; 6,810,606; 6,877,254; 6,918,197; 7,010,869; 7,082,697; 7,093,379; 7,127,834; 7,168,185; 7,174,658; 7,234,249; 7,287,341; 7,334,350; and 7,334,356 are hereby incorporated by reference herein in their entirety into this application for completeness of disclosure of the applicant's novel and useful combination of one or more of any of the features or components of any of the figures of this application with one or more of any of the features of any one or more of the preceding applicant's patents listed above in this paragraph to make new and useful improvements over the existing art.

The applicant's other footwear published U.S. Application Numbers 20020000051; 20020007571; 20020007572; 20020014020; 20020014021; 20020023373; 20020073578; 20020116841; 20030046830; 20030070320; 20030079375; 20030131497; 20030208926; 20030217482; 20040134096; 20040250447; 20050016020; 20050086837; 20050217143; 20060032086; 20060248749; 20070240332; 20070271817; 20080000108; 20080005931; and 20080022556 are hereby incorporated by reference herein in their entirety into this application for completeness of disclosure of the applicant's novel and useful combination of one or more of any of the features or components of any of the figures of this application with one or more of any of the features of any one or more of the preceding applicant's published U.S. Applications listed above in this paragraph to make new and useful improvements over the existing art.

The invention claimed is:

1. Orthotics or other footwear inserts for an intended wearer, comprising:
 a set of separate and incrementally different inserts each sized and adapted for a same standard size of a right and/or left foot of the intended wearer;

one said insert in said set having a first corrective structure and at least another said insert in said set having a second corrective structure that is incrementally different from the first corrective structure; as viewed in a frontal plane cross section taken at a same location of each of said inserts in said set, when said inserts in said set are upright and in an unloaded condition;

the second corrective structure including an incremental change in curvature of at least one sidemost portion of said insert in said set as compared to the first corrective structure and a corrective structure of each other said insert in said set, when viewed in a frontal plane cross-section when said orthotics or other footwear inserts are upright and in an unloaded condition, wherein said incremental change is one of an increase or decrease in curvature;

said inserts in said set having a progressive sequence based on the increase or decrease in the curvature of said at least one sidemost portion of each said insert in said set;

each said insert in said set including at least one internal sipe formed by internal surface portions of each said insert in said set, wherein the surface portions forming the at least one internal sipe oppose each other and move relative to each other in a sliding motion; and wherein said orthotics or other footwear inserts comprising each said insert in said set are adapted to be worn one at a time for a period of time using said inserts in said set sequentially based on the progressive sequence.

2. The orthotics or other footwear inserts of claim 1, wherein the at least one sidemost portion is configured to be located proximate to one or more of a first distal phalange, a head of a first metatarsal, a head of a fifth metatarsal, a base of a fifth metatarsal and a lateral tuberosity of a calcaneus of the intended wearer's foot when located in footwear including said orthotics or other footwear inserts.

3. The orthotics or other footwear inserts of claim 2, wherein inner and outer surfaces of said sidemost portion are curved concavely to define a concavely curved sidemost portion, as determined relative to a central portion of an intended wearer's foot location in the footwear including said orthotics or other footwear inserts, as viewed in a frontal plane cross-section when the footwear including said orthotics or other footwear inserts is upright and in an unloaded condition.

4. The orthotics or other footwear inserts of claim 1, further comprising a sole section including at least one inner compartment, chamber, or bladder, each inner compartment, chamber or bladder containing at least one fluid, and wherein at least a part of each of said at least one inner compartment, chamber or bladder is located in a single frontal plane cross-section of the shoe sole when the shoe sole is upright and in an unloaded condition;

at least one outer compartment, chamber, or bladder outside said inner compartment, chamber, or bladder; and said outer compartment, chamber, or bladder and said inner compartment, chamber, or bladder being separated at least in part by an internal sipe; and wherein said internal sipe is formed by at least a portion of an inner surface of said outer compartment, chamber, or bladder and at least a portion of an outer surface of each of said inner compartment, chamber, or bladder; and the inner and outer surface portions forming the sipe oppose each other and therefore can move relative to each other in a sliding motion.

5. The orthotics or other footwear inserts of claim 1, wherein said set of inserts includes at least five said separate inserts arranged in the progressive sequence.

6. The orthotics or other footwear inserts of claim 1, wherein said set of inserts comprises one subset of said inserts of said set for a right foot and one subset of said inserts of said set for a left foot and each of said inserts of said set is insertable into an outer sole by the intended wearer.

7. The orthotics or other footwear inserts of claim 2, including at least one said insert of said set that comprises one said corrective structure that is incrementally closer in one of curvature, thickness and firmness to the second corrective structure than the first corrective structure.

8. A set of separate and incrementally different footwear soles each sized and adapted for a same standard size of a right or left foot of the intended wearer;

one said footwear sole of said set comprising a first corrective structure and at least one other said footwear sole of said set comprising a second corrective structure that is incrementally different from the first corrective structure, as viewed in a frontal plane cross section taken at a same location of each of said footwear soles in said set when said footwear sole of said set is upright and in an unloaded condition;

each of said footwear soles of said set being sized and adapted for the standard size of a right or left foot of the intended wearer;

each of said footwear soles of said set including at least one internal sipe formed by internal surface portions of each said footwear sole of said set, wherein the surface portions forming the at least one internal sipe oppose each other and move relative to each other in a sliding motion;

the second corrective structure including an incremental change in curvature of at least one sidemost portion of each said footwear sole of said set as compared to the first corrective structure and a corrective structure of each other said footwear sole of said set, when viewed in a frontal plane cross-section when said footwear inserts are upright and in an unloaded condition, wherein said incremental change is one of an increase or decrease in curvature;

said footwear soles in said set having a progressive sequence based on the increase or decrease in the curvature of said at least one sidemost portion of each said footwear sole in said set; and wherein said footwear soles of said set are adapted to be worn one at a time for a period of time using said footwear soles in said set sequentially based on the progressive sequence.

9. The set of footwear soles of claim 8, wherein the at least one sidemost portion is configured to be located proximate to one or more of a first distal phalange, a head of a first metatarsal, a head of a fifth metatarsal, a base of a fifth metatarsal and a lateral tuberosity of a calcaneus of the intended wearer's foot when located in footwear being worn by the intended wearer.

10. The set of footwear soles of claim 9, wherein inner and outer surfaces of said sidemost portion are curved concavely to define a concavely curved sidemost portion, as determined relative to a central portion of an intended wearer's foot location in the footwear including said orthotics or other footwear inserts, as viewed in a frontal plane cross-section when the footwear is upright and in an unloaded condition.

11. The set of footwear soles of claim 8, further comprising a sole section including at least one inner compartment, chamber, or bladder, each inner compartment, chamber or bladder containing at least one fluid, and wherein at least a part of each of said at least one inner compartment, chamber or bladder is located in a single frontal plane cross-section of the shoe sole when the shoe sole is upright and in an unloaded condition;

at least one outer compartment, chamber, or bladder outside said inner compartment, chamber, or bladder; and said outer compartment, chamber, or bladder and said inner compartment, chamber, or bladder being separated at least in part by an internal sipe; and wherein said internal sipe is formed by at least a portion of an inner surface of said outer compartment, chamber, or bladder and at least a portion of an outer surface of each of said inner compartment, chamber, or bladder; and the inner and outer surface portions forming the sipe oppose each other and therefore can move relative to each other in a sliding motion.

12. The set of footwear soles of claim 9, wherein said set of footwear soles includes at least five said separate footwear soles of said set arranged in the progressive sequence.

13. The set of footwear soles of claim 8, wherein one said corrective structure of at least one said footwear sole of said set includes at least a change in curvature or firmness.

14. A set of integrated shoe soles and orthotics, each of said integrated shoe soles and orthotics comprising:

a shoe sole, and an orthotic, said integrated shoe soles and orthotics including at least one common material, each of said shoe soles in said set being adapted and sized for a same standard size of a left or right foot of an intended wearer;

each of said shoe soles in said set including at least one internal sipe formed by internal surface portions of each said shoe sole in said set, wherein the surface portions forming the at least one internal sipe oppose each other and move relative to each other in a sliding motion;

one said integrated shoe sole and orthotic having a first corrective structure and at least one said integrated shoe sole and orthotic having a corrective structure that is incrementally different from the first corrective structure, as viewed in a frontal plane cross section taken at a same location of each said integrated shoe sole and orthotic when said integrated shoe sole and orthotic is upright and in an unloaded condition;

each said corrective structure that is incrementally different from the first corrective structure including an incremental change in curvature of at least one sidemost portion of said integrated shoe sole and orthotic as compared to the first corrective structure and the corrective structure of each other said integrated shoe sole and orthotic when viewed in a frontal plane cross-section when said integrated shoe soles and orthotics are upright and in an unloaded condition, wherein said incremental change is one of an increase or decrease in curvature;

said set of integrated shoe soles and orthotics having a progressive sequence based on the increase or decrease in the curvature of said at least one sidemost portion of each said integrated shoe sole and orthotic; and wherein each said integrated shoe sole and orthotic is adapted to be worn one at a time for a period of time sequentially based on the progressive sequence.

15. The set of integrated shoe soles and orthotics of claim 14, wherein the at least one sidemost portion is configured to be located proximate to one or more of a first distal phalange, a head of a first metatarsal, a head of a fifth metatarsal, a base of a fifth metatarsal and a lateral tuberosity of a calcaneus of the intended wearer's foot when located in footwear.

16. The set of integrated shoe soles and orthotics of claim 15, wherein inner and outer surfaces of said sidemost portion are curved concavely to define a concavely curved sidemost portion, as determined relative to a central portion of an intended wearer's foot location in the footwear including said orthotics or other footwear inserts, as viewed in a frontal plane cross-section when the footwear including said orthotics or other footwear inserts is upright and in an unloaded condition.

17. The set of integrated shoe soles and orthotics of claim 14, further comprising a sole section including at least one inner compartment, chamber, or bladder, each inner compartment, chamber or bladder containing at least one fluid, and wherein at least a part of each of said at least one inner compartment, chamber or bladder is located in a single frontal plane cross-section of the shoe sole when the shoe sole is upright and in an unloaded condition;

at least one outer compartment, chamber, or bladder outside said inner compartment, chamber, or bladder; and said outer compartment, chamber, or bladder and said inner compartment, chamber, or bladder being separated at least in part by an internal sipe; and wherein said internal sipe is formed by at least a portion of an inner surface of said outer compartment, chamber, or bladder and at least a portion of an outer surface of each of said inner compartment, chamber, or bladder; and the inner and outer surface portions forming the sipe oppose each other and therefore can move relative to each other in a sliding motion.

18. The set of integrated shoe soles and orthotics of claim 14, wherein an inner surface and an outer surface of at least two said footwear soles of said set are substantially parallel to each other between a position proximate to a lateral sidemost extent and a position proximate to a medial sidemost extent, as viewed in at least one frontal plane cross section when said at least two footwear soles of said set are upright and in an unloaded condition.

19. The orthotics or other footwear inserts of claim 1, wherein at least one said insert of said set includes one said corrective structure having at least a change in curvature or firmness.

20. The set of integrated shoe soles and orthotics of claim 14, wherein at least one said shoe sole of said set includes one said corrective structure having at least a change in curvature or firmness.

21. The orthotics or other footwear inserts of claim 1, wherein said corrective structures are configured to correct at least one problem with at least one foot of the intended wearer selected from flat foot, a hammer toe deformity and bilateral asymmetry.

22. The set of footwear soles of claim 8, wherein said corrective structures are configured to correct at least one problem with at least one foot of the intended wearer selected from flat foot, a hammer toe deformity and bilateral asymmetry.

23. The set of integrated shoe soles and orthotics of claim 14, wherein said corrective structures are configured to correct at least one problem with at least one foot of the intended wearer selected from flat foot, a hammer toe deformity and bilateral asymmetry.

* * * * *